United States Patent
Schott

(10) Patent No.: US 8,561,795 B2
(45) Date of Patent: Oct. 22, 2013

(54) LOW-PRESSURE PACKAGING FOR FLUID DEVICES

(71) Applicant: Kevin Schott, Southampton, MA (US)

(72) Inventor: Kevin Schott, Southampton, MA (US)

(73) Assignee: Seventh Sense Biosystems, Inc., Cambridge, MA (US)

( * ) Notice: Subject to any disclaimer, the term of this patent is extended or adjusted under 35 U.S.C. 154(b) by 0 days.

(21) Appl. No.: 13/678,316

(22) Filed: Nov. 15, 2012

(65) Prior Publication Data

US 2013/0081960 A1   Apr. 4, 2013

Related U.S. Application Data

(63) Continuation of application No. 13/183,789, filed on Jul. 15, 2011.

(60) Provisional application No. 61/365,196, filed on Jul. 16, 2010.

(51) Int. Cl.
*A61B 17/06* (2006.01)
*B65D 81/24* (2006.01)

(52) U.S. Cl.
USPC ............ 206/439; 206/438; 206/210; 206/207

(58) Field of Classification Search
USPC .......... 206/363, 210, 213.1, 438, 524.8, 439, 206/207
See application file for complete search history.

(56) References Cited

U.S. PATENT DOCUMENTS

| | | | |
|---|---|---|---|
| 3,060,429 A | 10/1962 | Winston | |
| 3,339,546 A | 9/1967 | Chen | |
| 3,551,554 A | 12/1970 | Herschler | |
| 3,711,602 A | 1/1973 | Herschler | |
| 3,711,606 A | 1/1973 | Herschler | |

(Continued)

FOREIGN PATENT DOCUMENTS

| CN | 1222334 A | 7/1990 |
|---|---|---|
| CN | 1753646 A | 3/2006 |

(Continued)

OTHER PUBLICATIONS

International Preliminary Report on Patentability for PCT/US2011/043698 mailed Feb. 7, 2013.
International Search Report and Written Opinion for PCT/US2011/044145 mailed Dec. 2, 2011.
International Search Report and Written Opinion for PCT/US2011/047565 mailed Mar. 9, 2012.

(Continued)

*Primary Examiner* — Emily Schmidt
*Assistant Examiner* — Bradley G Thomas, Jr.
(74) *Attorney, Agent, or Firm* — Wolf, Greenfield & Sacks, P.C.

(57) ABSTRACT

Certain aspects of the invention are generally directed to devices for withdrawing a substance from the skin and/or from beneath the skin of a subject, and/or for delivering a substance to the skin and/or to a location beneath the skin of a subject. In some embodiments, the devices may comprise one or more skin insertion objects, such as needles or microneedles. In some cases, the device also may comprise one or more vacuum chambers. In some aspects, the device may be contained within an environment able to assist with maintenance of such pressures. For example, a package containing such an environment may also have a pressure less than atmospheric pressure, and/or the package may be molded to the device or otherwise have a shape that does not contain substantial gases that can "leak" into the device and alter the pressure of any vacuum chambers that may be contained therein.

16 Claims, 4 Drawing Sheets

(56) References Cited

U.S. PATENT DOCUMENTS

| | | | |
|---|---|---|---|
| 3,740,421 A | 6/1973 | Schmolka | |
| 3,908,657 A | 9/1975 | Kowarski | |
| 4,103,684 A | 8/1978 | Ismach | |
| 4,150,744 A * | 4/1979 | Fennimore | 206/205 |
| 4,253,460 A | 3/1981 | Chen et al. | |
| 4,329,999 A | 5/1982 | Phillips | |
| 4,537,776 A | 8/1985 | Cooper | |
| 4,553,552 A | 11/1985 | Valdespino et al. | |
| 4,557,943 A | 12/1985 | Rosler et al. | |
| 4,615,697 A | 10/1986 | Robinson | |
| 4,621,268 A | 11/1986 | Keeling et al. | |
| 4,637,403 A | 1/1987 | Garcia et al. | |
| 4,696,309 A | 9/1987 | Stephan | |
| 4,706,676 A | 11/1987 | Peck | |
| 4,740,365 A | 4/1988 | Yukimatsu et al. | |
| 4,756,314 A | 7/1988 | Eckenhoff et al. | |
| 4,764,378 A | 8/1988 | Keith et al. | |
| 4,772,470 A | 9/1988 | Inoue et al. | |
| 4,820,720 A | 4/1989 | Sanders et al. | |
| 4,821,733 A | 4/1989 | Peck | |
| 4,855,298 A | 8/1989 | Yamada et al. | |
| 4,863,970 A | 9/1989 | Patel et al. | |
| 4,908,404 A | 3/1990 | Benedict et al. | |
| 4,957,108 A | 9/1990 | Schoendorfer et al. | |
| 4,973,468 A | 11/1990 | Chiang et al. | |
| 5,006,342 A | 4/1991 | Cleary et al. | |
| 5,015,677 A | 5/1991 | Benedict et al. | |
| 5,036,861 A | 8/1991 | Sembrowich et al. | |
| 5,054,499 A | 10/1991 | Swierczek | |
| 5,076,273 A | 12/1991 | Schoendorfer et al. | |
| 5,161,532 A | 11/1992 | Joseph | |
| 5,174,291 A | 12/1992 | Schoonen et al. | |
| 5,201,324 A | 4/1993 | Swierczek | |
| 5,213,568 A | 5/1993 | Lattin et al. | |
| 5,231,993 A | 8/1993 | Haber et al. | |
| 5,279,294 A | 1/1994 | Anderson et al. | |
| 5,320,607 A | 6/1994 | Ishibashi | |
| 5,402,798 A | 4/1995 | Swierczek et al. | |
| 5,438,984 A | 8/1995 | Schoendorfer | |
| 5,441,048 A | 8/1995 | Schoendorfer | |
| 5,441,490 A | 8/1995 | Svedman | |
| 5,443,080 A | 8/1995 | D'Angelo et al. | |
| 5,445,611 A | 8/1995 | Eppstein et al. | |
| 5,458,140 A | 10/1995 | Eppstein et al. | |
| 5,505,212 A | 4/1996 | Keljmann et al. | |
| 5,507,288 A | 4/1996 | Bocker et al. | |
| 5,520,727 A | 5/1996 | Vreeland et al. | |
| 5,529,581 A | 6/1996 | Cusack | |
| 5,560,543 A | 10/1996 | Smith et al. | |
| 5,574,134 A | 11/1996 | Waite | |
| 5,580,794 A | 12/1996 | Allen | |
| 5,582,184 A | 12/1996 | Erickson et al. | |
| 5,636,640 A * | 6/1997 | Staehlin | 600/577 |
| 5,638,815 A | 6/1997 | Schoendorfer | |
| 5,662,127 A | 9/1997 | De Vaughn | |
| 5,676,144 A | 10/1997 | Schoendorfer | |
| 5,680,872 A | 10/1997 | Sesekura et al. | |
| 5,682,233 A | 10/1997 | Brinda | |
| 5,685,875 A | 11/1997 | Hlavinka et al. | |
| 5,714,390 A | 2/1998 | Hallowitz et al. | |
| 5,741,138 A | 4/1998 | Rice et al. | |
| 5,746,217 A | 5/1998 | Erickson et al. | |
| 5,800,420 A | 9/1998 | Gross et al. | |
| 5,807,375 A | 9/1998 | Gross et al. | |
| 5,811,108 A | 9/1998 | Goeringer | |
| 5,813,614 A | 9/1998 | Coffee | |
| 5,817,011 A | 10/1998 | Schoendorfer | |
| 5,817,012 A | 10/1998 | Schoendorfer | |
| 5,820,570 A | 10/1998 | Erickson et al. | |
| 5,820,622 A | 10/1998 | Gross et al. | |
| 5,823,973 A | 10/1998 | Racchini et al. | |
| 5,857,983 A | 1/1999 | Douglas et al. | |
| 5,858,188 A | 1/1999 | Soane et al. | |
| 5,873,900 A | 2/1999 | Maurer et al. | |
| 5,876,675 A | 3/1999 | Kennedy | |
| 5,879,310 A | 3/1999 | Sopp et al. | |
| 5,879,311 A | 3/1999 | Duchon et al. | |
| 5,879,367 A | 3/1999 | Latterell et al. | |
| 5,885,211 A | 3/1999 | Eppstein et al. | |
| 5,891,053 A | 4/1999 | Sesekura | |
| 5,944,662 A | 8/1999 | Schoendorfer | |
| 5,951,492 A | 9/1999 | Douglas et al. | |
| 5,951,493 A | 9/1999 | Douglas et al. | |
| 5,955,096 A | 9/1999 | Santos et al. | |
| 5,963,136 A | 10/1999 | O'Brien | |
| 5,964,718 A | 10/1999 | Duchon et al. | |
| 5,985,312 A | 11/1999 | Jacob et al. | |
| 5,998,588 A | 12/1999 | Hoffman et al. | |
| 6,007,845 A | 12/1999 | Domb et al. | |
| 6,015,392 A | 1/2000 | Douglas et al. | |
| 6,027,459 A | 2/2000 | Shain et al. | |
| 6,044,303 A | 3/2000 | Agarwala et al. | |
| 6,048,337 A | 4/2000 | Svedman | |
| 6,050,988 A | 4/2000 | Zuck | |
| 6,063,029 A | 5/2000 | Saita et al. | |
| 6,063,039 A | 5/2000 | Cunningham et al. | |
| 6,063,365 A | 5/2000 | Shefer et al. | |
| 6,066,103 A | 5/2000 | Duchon et al. | |
| 6,071,249 A | 6/2000 | Cunningham et al. | |
| 6,071,250 A | 6/2000 | Douglas et al. | |
| 6,071,251 A | 6/2000 | Cunningham et al. | |
| 6,080,116 A | 6/2000 | Erickson et al. | |
| 6,083,196 A | 7/2000 | Trautman et al. | |
| 6,091,975 A | 7/2000 | Daddona et al. | |
| 6,093,156 A | 7/2000 | Cunningham et al. | |
| 6,099,484 A | 8/2000 | Douglas et al. | |
| 6,107,102 A | 8/2000 | Ferrari | |
| 6,126,899 A | 10/2000 | Woudenberg et al. | |
| 6,132,449 A | 10/2000 | Lum et al. | |
| 6,132,702 A | 10/2000 | Witt et al. | |
| 6,152,889 A | 11/2000 | Sopp et al. | |
| 6,155,992 A | 12/2000 | Henning et al. | |
| 6,162,639 A | 12/2000 | Douglas | |
| 6,190,315 B1 | 2/2001 | Kost et al. | |
| 6,192,890 B1 | 2/2001 | Levy et al. | |
| 6,203,504 B1 | 3/2001 | Latterell et al. | |
| 6,206,841 B1 | 3/2001 | Cunningham et al. | |
| 6,219,574 B1 | 4/2001 | Cormier et al. | |
| 6,228,100 B1 | 5/2001 | Schraga | |
| 6,230,051 B1 | 5/2001 | Cormier et al. | |
| 6,234,990 B1 | 5/2001 | Rowe et al. | |
| 6,235,313 B1 | 5/2001 | Mathiowitz et al. | |
| 6,252,129 B1 | 6/2001 | Coffee | |
| 6,267,724 B1 | 7/2001 | Taylor | |
| 6,283,926 B1 | 9/2001 | Cunningham et al. | |
| 6,306,104 B1 | 10/2001 | Cunningham et al. | |
| 6,306,993 B1 | 10/2001 | Rothbard et al. | |
| 6,319,210 B1 | 11/2001 | Douglas et al. | |
| 6,322,574 B1 | 11/2001 | Lloyd | |
| 6,332,871 B1 | 12/2001 | Douglas et al. | |
| 6,334,856 B1 | 1/2002 | Allen et al. | |
| 6,340,354 B1 | 1/2002 | Rambin | |
| 6,349,229 B1 | 2/2002 | Watanabe et al. | |
| 6,361,944 B1 | 3/2002 | Mirkin et al. | |
| 6,364,890 B1 | 4/2002 | Lum et al. | |
| 6,379,324 B1 | 4/2002 | Gartstein et al. | |
| 6,391,471 B1 | 5/2002 | Hiraoka et al. | |
| 6,406,919 B1 | 6/2002 | Tyrrell | |
| 6,409,679 B2 | 6/2002 | Pyo | |
| 6,436,078 B1 | 8/2002 | Svedman | |
| 6,440,096 B1 | 8/2002 | Lastovich et al. | |
| 6,455,324 B1 | 9/2002 | Douglas | |
| 6,461,644 B1 | 10/2002 | Jackson et al. | |
| 6,464,649 B1 | 10/2002 | Duchon et al. | |
| 6,465,002 B1 | 10/2002 | Mathiowitz et al. | |
| 6,485,439 B1 | 11/2002 | Roe et al. | |
| 6,485,703 B1 | 11/2002 | Cote et al. | |
| 6,491,657 B2 | 12/2002 | Rowe et al. | |
| 6,491,902 B2 | 12/2002 | Shefer et al. | |
| 6,501,976 B1 | 12/2002 | Sohrab | |
| 6,502,697 B1 * | 1/2003 | Crampton et al. | 206/484 |
| 6,503,209 B2 | 1/2003 | Hakky et al. | |
| 6,503,231 B1 | 1/2003 | Prausnitz et al. | |
| 6,506,168 B1 | 1/2003 | Fathallah et al. | |

(56) References Cited

U.S. PATENT DOCUMENTS

| | | | |
|---|---|---|---|
| 6,527,716 B1 | 3/2003 | Eppstein |
| 6,532,386 B2 | 3/2003 | Sun et al. |
| 6,537,243 B1 | 3/2003 | Henning et al. |
| 6,537,264 B1 | 3/2003 | Cormier et al. |
| 6,538,089 B1 | 3/2003 | Samra et al. |
| 6,540,675 B2 | 4/2003 | Aceti et al. |
| 6,548,264 B1 | 4/2003 | Tan et al. |
| 6,558,361 B1 | 5/2003 | Yeshurun |
| 6,562,014 B2 | 5/2003 | Lin et al. |
| 6,589,562 B1 | 7/2003 | Shefer et al. |
| 6,591,124 B2 | 7/2003 | Sherman et al. |
| 6,602,205 B1 | 8/2003 | Erickson et al. |
| 6,603,987 B2 | 8/2003 | Whitson |
| 6,607,495 B1 | 8/2003 | Skalak et al. |
| 6,607,513 B1 | 8/2003 | Down et al. |
| 6,611,707 B1 | 8/2003 | Prausnitz et al. |
| 6,614,522 B1 | 9/2003 | Sopp et al. |
| 6,620,123 B1 | 9/2003 | Mitragotri et al. |
| 6,624,882 B2 | 9/2003 | Sopp et al. |
| 6,652,478 B1 | 11/2003 | Gartstein et al. |
| 6,669,961 B2 | 12/2003 | Kim et al. |
| 6,678,554 B1 | 1/2004 | Sun et al. |
| 6,685,921 B2 | 2/2004 | Lawlor |
| 6,689,100 B2 | 2/2004 | Connelly et al. |
| 6,696,075 B2 | 2/2004 | Mathiowitz et al. |
| 6,706,000 B2 | 3/2004 | Perez et al. |
| 6,706,159 B2 | 3/2004 | Moerman et al. |
| 6,712,776 B2 | 3/2004 | Latterell et al. |
| 6,743,211 B1 | 6/2004 | Prausnitz et al. |
| 6,749,575 B2 | 6/2004 | Matriano et al. |
| 6,765,081 B2 | 7/2004 | Lin et al. |
| 6,766,817 B2 | 7/2004 | da Silva |
| 6,768,920 B2 | 7/2004 | Lange et al. |
| 6,783,502 B2 | 8/2004 | Orloff et al. |
| 6,786,874 B2 | 9/2004 | Grace et al. |
| 6,793,633 B2 | 9/2004 | Douglas et al. |
| 6,798,920 B1 | 9/2004 | Wells et al. |
| 6,800,122 B2 | 10/2004 | Anderson et al. |
| 6,811,090 B2 | 11/2004 | Yogi et al. |
| 6,814,760 B2 | 11/2004 | Anderson et al. |
| 6,825,161 B2 | 11/2004 | Shefer et al. |
| 6,826,426 B2 | 11/2004 | Lange et al. |
| 6,837,858 B2 | 1/2005 | Cunningham et al. |
| 6,855,133 B2 | 2/2005 | Svedman |
| 6,860,873 B2 | 3/2005 | Allen et al. |
| 6,878,120 B2 | 4/2005 | Roe et al. |
| 6,899,851 B2 | 5/2005 | Allen et al. |
| 6,908,448 B2 | 6/2005 | Redding, Jr. |
| 6,918,404 B2 | 7/2005 | Dias da Silva |
| 6,918,901 B1 | 7/2005 | Theeuwes et al. |
| 6,923,764 B2 | 8/2005 | Aceti et al. |
| 6,931,277 B1 | 8/2005 | Yuzhakov et al. |
| 6,940,591 B2 | 9/2005 | Sopp et al. |
| 6,952,604 B2 | 10/2005 | DeNuzzio et al. |
| 6,969,359 B2 | 11/2005 | Duchon et al. |
| 6,990,367 B2 | 1/2006 | Kiser et al. |
| 6,997,886 B2 | 2/2006 | Latterell et al. |
| 7,001,343 B2 | 2/2006 | Erickson et al. |
| 7,001,344 B2 | 2/2006 | Freeman et al. |
| 7,004,928 B2 | 2/2006 | Aceti et al. |
| 7,008,384 B2 | 3/2006 | Tapper |
| 7,014,615 B2 | 3/2006 | Erickson et al. |
| 7,037,277 B1 | 5/2006 | Smith et al. |
| 7,041,067 B2 | 5/2006 | Sopp et al. |
| 7,041,068 B2 | 5/2006 | Freeman et al. |
| 7,047,070 B2 | 5/2006 | Wilkinson et al. |
| 7,066,586 B2 | 6/2006 | da Silva |
| 7,066,885 B2 | 6/2006 | Erickson et al. |
| 7,097,631 B2 | 8/2006 | Trautman et al. |
| 7,133,717 B2 | 11/2006 | Coston et al. |
| 7,137,957 B2 | 11/2006 | Erickson et al. |
| 7,150,755 B2 | 12/2006 | Levaughn et al. |
| 7,174,199 B2 | 2/2007 | Berner et al. |
| 7,182,910 B2 | 2/2007 | Allen et al. |
| 7,235,056 B2 | 6/2007 | Duchon et al. |
| 7,247,144 B2 | 7/2007 | Douglas et al. |
| 7,264,627 B2 | 9/2007 | Perez |
| 7,344,499 B1 | 3/2008 | Prausnitz et al. |
| 7,344,587 B2 | 3/2008 | Khan et al. |
| 7,374,545 B2 | 5/2008 | Alroy |
| 7,374,949 B2 | 5/2008 | Kuriger |
| 7,402,441 B2 | 7/2008 | Lowe et al. |
| 7,413,868 B2 | 8/2008 | Kauvar et al. |
| 7,429,258 B2 | 9/2008 | Angel et al. |
| 7,544,185 B2 | 6/2009 | Bengtsson |
| 7,585,278 B2 | 9/2009 | Aceti et al. |
| 7,585,412 B2 | 9/2009 | Gorsuch et al. |
| 7,631,760 B2 * | 12/2009 | Guelzow et al. .............. 206/438 |
| 7,767,017 B2 | 8/2010 | Lahann et al. |
| 7,811,302 B2 | 10/2010 | Steg |
| 7,896,830 B2 | 3/2011 | Gura et al. |
| 7,942,827 B2 | 5/2011 | Mir et al. |
| 7,947,772 B2 | 5/2011 | Lahann |
| 8,043,480 B2 | 10/2011 | Lahann et al. |
| 8,052,849 B2 | 11/2011 | Lahann et al. |
| 8,133,191 B2 | 3/2012 | Rosenberg et al. |
| 8,187,708 B2 | 5/2012 | Lahann et al. |
| 8,202,240 B2 | 6/2012 | Felt et al. |
| 8,344,028 B2 | 1/2013 | Xu et al. |
| 2001/0005772 A1 | 6/2001 | Kisakibaru |
| 2002/0010414 A1 | 1/2002 | Coston et al. |
| 2002/0013538 A1 | 1/2002 | Teller |
| 2002/0065453 A1 | 5/2002 | Lesho et al. |
| 2002/0077584 A1 | 6/2002 | Lin et al. |
| 2002/0082543 A1 | 6/2002 | Park et al. |
| 2002/0099308 A1 | 7/2002 | Bojan et al. |
| 2002/0099356 A1 | 7/2002 | Unger et al. |
| 2002/0130042 A1 | 9/2002 | Moerman et al. |
| 2002/0138049 A1 | 9/2002 | Allen |
| 2002/0168290 A1 | 11/2002 | Yuzhakov et al. |
| 2002/0169393 A1 | 11/2002 | Cunningham et al. |
| 2002/0169394 A1 | 11/2002 | Eppstein et al. |
| 2002/0169411 A1 | 11/2002 | Sherman et al. |
| 2002/0187556 A1 | 12/2002 | Shartle et al. |
| 2002/0188221 A1 | 12/2002 | Sohrab |
| 2003/0040682 A1 | 2/2003 | Tapper |
| 2003/0055326 A1 | 3/2003 | Sohrab |
| 2003/0100846 A1 | 5/2003 | Custer et al. |
| 2003/0113540 A1 | 6/2003 | Anderson et al. |
| 2003/0135158 A1 | 7/2003 | Gonnelli |
| 2003/0135167 A1 | 7/2003 | Gonnelli |
| 2003/0135201 A1 | 7/2003 | Gonnelli |
| 2003/0143746 A1 | 7/2003 | Sage |
| 2003/0159615 A1 | 8/2003 | Anderson et al. |
| 2003/0181863 A1 | 9/2003 | Ackley et al. |
| 2003/0195398 A1 | 10/2003 | Suzuki et al. |
| 2003/0204148 A1 | 10/2003 | Lange et al. |
| 2003/0208138 A1 | 11/2003 | Olson |
| 2003/0212344 A1 | 11/2003 | Yuzhakov et al. |
| 2003/0212345 A1 | 11/2003 | McAllister et al. |
| 2003/0212347 A1 | 11/2003 | Sohrab |
| 2003/0212423 A1 | 11/2003 | Pugh et al. |
| 2003/0228367 A1 | 12/2003 | Mathiowitz et al. |
| 2004/0010207 A1 | 1/2004 | Flaherty et al. |
| 2004/0058458 A1 | 3/2004 | Anker et al. |
| 2004/0096959 A1 | 5/2004 | Stiene et al. |
| 2004/0098009 A1 | 5/2004 | Boecker et al. |
| 2004/0106904 A1 | 6/2004 | Gonnelli et al. |
| 2004/0171980 A1 | 9/2004 | Mitragotri et al. |
| 2004/0199103 A1 | 10/2004 | Kwon |
| 2004/0204744 A1 | 10/2004 | Penner et al. |
| 2004/0236250 A1 | 11/2004 | Hodges et al. |
| 2004/0247016 A1 | 12/2004 | Faries et al. |
| 2004/0249310 A1 | 12/2004 | Shartle et al. |
| 2004/0253185 A1 | 12/2004 | Herweck et al. |
| 2005/0015055 A1 | 1/2005 | Yang |
| 2005/0019902 A1 | 1/2005 | Mathies et al. |
| 2005/0027176 A1 | 2/2005 | Xie |
| 2005/0027308 A1 | 2/2005 | Davis et al. |
| 2005/0054907 A1 | 3/2005 | Page et al. |
| 2005/0064529 A1 | 3/2005 | Kwon |
| 2005/0069925 A1 | 3/2005 | Ford et al. |
| 2005/0070819 A1 | 3/2005 | Poux et al. |
| 2005/0085838 A1 | 4/2005 | Thompson et al. |

(56) References Cited

U.S. PATENT DOCUMENTS

| | | |
|---|---|---|
| 2005/0106066 A1 | 5/2005 | Saltsman et al. |
| 2005/0137536 A1 | 6/2005 | Gonnelli |
| 2005/0172852 A1 | 8/2005 | Anderson et al. |
| 2005/0182307 A1 | 8/2005 | Currie et al. |
| 2005/0196747 A1 | 9/2005 | Stiene |
| 2005/0201974 A1 | 9/2005 | Schestopol et al. |
| 2005/0203360 A1 | 9/2005 | Brauker et al. |
| 2005/0221276 A1 | 10/2005 | Rozakis et al. |
| 2005/0228313 A1 | 10/2005 | Kaler et al. |
| 2005/0245844 A1 | 11/2005 | Mace et al. |
| 2005/0249672 A1 | 11/2005 | Bolbot |
| 2005/0251152 A1 | 11/2005 | Herweck et al. |
| 2005/0261632 A1 | 11/2005 | Xu |
| 2005/0261639 A1 | 11/2005 | Herweck |
| 2006/0001551 A1 | 1/2006 | Kraft et al. |
| 2006/0004271 A1 | 1/2006 | Peyser et al. |
| 2006/0030790 A1 | 2/2006 | Braig et al. |
| 2006/0036187 A1 | 2/2006 | Vos et al. |
| 2006/0058602 A1 | 3/2006 | Kwiatkowski et al. |
| 2006/0142651 A1 | 6/2006 | Brister et al. |
| 2006/0200046 A1 | 9/2006 | Windus-Smith et al. |
| 2006/0228259 A1 | 10/2006 | Samsoondar |
| 2007/0004989 A1 | 1/2007 | Dhillon |
| 2007/0016446 A1 | 1/2007 | Brown |
| 2007/0027427 A1 | 2/2007 | Trautman et al. |
| 2007/0031283 A1 | 2/2007 | Davis et al. |
| 2007/0046476 A1 | 3/2007 | Hinkamp |
| 2007/0054119 A1 | 3/2007 | Garstecki et al. |
| 2007/0066934 A1 | 3/2007 | Etheredge et al. |
| 2007/0078414 A1 | 4/2007 | McAllister et al. |
| 2007/0092637 A1 | 4/2007 | Brown et al. |
| 2007/0100219 A1 | 5/2007 | Sweitzer et al. |
| 2007/0105176 A1 | 5/2007 | Ibey et al. |
| 2007/0112180 A1 | 5/2007 | Gray et al. |
| 2007/0123801 A1 | 5/2007 | Goldberger et al. |
| 2007/0129618 A1 | 6/2007 | Goldberger et al. |
| 2007/0161964 A1 | 7/2007 | Yuzhakov |
| 2007/0167340 A1 | 7/2007 | Barthel et al. |
| 2007/0179404 A1 | 8/2007 | Escutia et al. |
| 2007/0185432 A1 | 8/2007 | Etheredge et al. |
| 2007/0208275 A1 | 9/2007 | Vinogradov et al. |
| 2007/0213638 A1 | 9/2007 | Herbrechtsmeier et al. |
| 2007/0231355 A1 | 10/2007 | Quadir et al. |
| 2007/0232956 A1 | 10/2007 | Harman et al. |
| 2007/0233199 A1 | 10/2007 | Moore et al. |
| 2007/0237800 A1 | 10/2007 | Lahann |
| 2007/0238943 A1 | 10/2007 | Poulsen et al. |
| 2008/0014627 A1 | 1/2008 | Merchant et al. |
| 2008/0077430 A1 | 3/2008 | Singer et al. |
| 2008/0081695 A1 | 4/2008 | Patchen |
| 2008/0086051 A1 | 4/2008 | Voegele |
| 2008/0099478 A1 | 5/2008 | Gleich |
| 2008/0112886 A1 | 5/2008 | Mitragotri et al. |
| 2008/0125743 A1 | 5/2008 | Yuzhakov |
| 2008/0129486 A1 | 6/2008 | Jeckelman et al. |
| 2008/0140049 A1 | 6/2008 | Kirby |
| 2008/0154107 A1 | 6/2008 | Jina |
| 2008/0167535 A1 | 7/2008 | Stivoric et al. |
| 2008/0167613 A1 | 7/2008 | Khouri et al. |
| 2008/0183144 A1 | 7/2008 | Trautmann et al. |
| 2008/0200838 A1 | 8/2008 | Goldberger et al. |
| 2008/0220411 A1 | 9/2008 | McNaughton et al. |
| 2008/0221407 A1 | 9/2008 | Baker |
| 2008/0269666 A1 | 10/2008 | Wang et al. |
| 2008/0275327 A1 | 11/2008 | Faarbaek et al. |
| 2008/0281290 A1 | 11/2008 | Yodfat et al. |
| 2008/0300508 A1 | 12/2008 | Tomer |
| 2009/0036795 A1 | 2/2009 | Duineveld et al. |
| 2009/0043250 A1 | 2/2009 | Gonnelli |
| 2009/0099478 A1 | 4/2009 | Cassells et al. |
| 2009/0099529 A1 | 4/2009 | Anderson et al. |
| 2009/0105614 A1 | 4/2009 | Momose et al. |
| 2009/0182306 A1 | 7/2009 | Lee et al. |
| 2009/0187160 A1 | 7/2009 | McAllister et al. |
| 2009/0198189 A1 | 8/2009 | Simons et al. |
| 2009/0216103 A1 | 8/2009 | Brister et al. |
| 2009/0216629 A1 | 8/2009 | James et al. |
| 2009/0264720 A1 | 10/2009 | Torjman et al. |
| 2009/0318846 A1 | 12/2009 | Prausnitz et al. |
| 2010/0042137 A1 | 2/2010 | Oronsky et al. |
| 2010/0049126 A1 | 2/2010 | Bronfeld et al. |
| 2010/0069726 A1 | 3/2010 | Levinson |
| 2010/0111970 A1 | 5/2010 | Pons et al. |
| 2010/0121368 A1 | 5/2010 | Kim et al. |
| 2010/0147763 A1 | 6/2010 | Tsou et al. |
| 2010/0160894 A1 | 6/2010 | Julian et al. |
| 2010/0249560 A1 | 9/2010 | Levinson et al. |
| 2010/0256465 A1 | 10/2010 | Bernstein et al. |
| 2010/0256524 A1 | 10/2010 | Levinson et al. |
| 2010/0261988 A1 | 10/2010 | Tamir |
| 2010/0269837 A1 | 10/2010 | Levinson et al. |
| 2010/0272652 A1 | 10/2010 | Levinson et al. |
| 2010/0324449 A1 | 12/2010 | Rostaing et al. |
| 2010/0324451 A1 | 12/2010 | Ishibashi et al. |
| 2011/0003770 A1 | 1/2011 | Eek |
| 2011/0009847 A1 | 1/2011 | Levinson et al. |
| 2011/0105828 A1 | 5/2011 | Perless et al. |
| 2011/0105872 A1 | 5/2011 | Chickering et al. |
| 2011/0105951 A1 | 5/2011 | Bernstein et al. |
| 2011/0105952 A1 | 5/2011 | Bernstein et al. |
| 2011/0125058 A1 | 5/2011 | Levinson et al. |
| 2011/0172508 A1 | 7/2011 | Chickering, III et al. |
| 2011/0172510 A1 | 7/2011 | Chickering, III et al. |
| 2011/0181410 A1 | 7/2011 | Levinson et al. |
| 2011/0245708 A1 | 10/2011 | Finkel et al. |
| 2011/0251562 A1 | 10/2011 | Chickering, III et al. |
| 2011/0288389 A9 | 11/2011 | Levinson et al. |
| 2012/0010529 A1 | 1/2012 | Chickering, III et al. |
| 2012/0016308 A1 | 1/2012 | Schott |
| 2012/0039809 A1 | 2/2012 | Levinson et al. |
| 2012/0041338 A1 | 2/2012 | Chickering et al. |
| 2012/0123297 A1 | 5/2012 | Brancazio |
| 2012/0271125 A1 | 10/2012 | Bernstein et al. |
| 2012/0275955 A1 | 11/2012 | Haghgooie et al. |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2012/0315271 A1 | 12/2012 | Shelton et al. |
| 2013/0018279 A1 | 1/2013 | Plante et al. |
| 2013/0079666 A1 | 3/2013 | Gonzalez-Zugasti et al. |
| 2013/0158468 A1 | 6/2013 | Bernstein et al. |
| 2013/0158482 A1 | 6/2013 | Davis et al. |

FOREIGN PATENT DOCUMENTS

| | | |
|---|---|---|
| DE | 198 33 868 A1 | 5/2000 |
| DE | 20 2008 010918 U1 | 12/2008 |
| EP | 0 043 738 A2 | 1/1982 |
| EP | 0 115 388 A1 | 8/1984 |
| EP | 0 250 693 A1 | 1/1988 |
| EP | 0 365 196 A2 | 4/1990 |
| EP | 0 555 554 A1 | 8/1993 |
| EP | 0 803 288 A2 | 10/1997 |
| EP | 0 838 232 A2 | 4/1998 |
| EP | 0 977 032 A1 | 2/2000 |
| EP | 1 360 934 A1 | 11/2003 |
| EP | 1 437 093 A1 | 7/2004 |
| EP | 1 470 781 A2 | 10/2004 |
| EP | 1 491 143 A1 | 12/2004 |
| EP | 1 522 260 A1 | 4/2005 |
| EP | 1 611 837 A2 | 1/2006 |
| EP | 1639938 A1 | 3/2006 |
| EP | 1 652 551 A2 | 5/2006 |
| EP | 1 834 589 A2 | 9/2007 |
| EP | 1 844 710 A1 | 10/2007 |
| EP | 1 997 431 A1 | 12/2008 |
| EP | 2 064 993 A1 | 6/2009 |
| EP | 2 077 128 A1 | 7/2009 |
| GB | 2153223 A | 8/1985 |
| JP | 2005-011364 A | 1/2005 |
| WO | WO 92/02175 A1 | 2/1992 |
| WO | WO 95/10223 A2 | 4/1995 |
| WO | WO 95/15783 A1 | 6/1995 |
| WO | WO 97/08987 A1 | 3/1997 |

(56) References Cited

FOREIGN PATENT DOCUMENTS

| | | |
|---|---|---|
| WO | WO 97/10745 A1 | 3/1997 |
| WO | WO 97/34587 A2 | 9/1997 |
| WO | WO 97/48442 A1 | 12/1997 |
| WO | WO 98/24366 A1 | 6/1998 |
| WO | WO 99/27852 A1 | 6/1999 |
| WO | WO 00/35357 A1 | 6/2000 |
| WO | WO 00/35530 A1 | 6/2000 |
| WO | WO 00/74763 A2 | 12/2000 |
| WO | WO 01/43643 A1 | 6/2001 |
| WO | WO 01/93946 A1 | 12/2001 |
| WO | WO 02/00101 A2 | 1/2002 |
| WO | WO 02/05890 A2 | 1/2002 |
| WO | WO 02/30506 A2 | 4/2002 |
| WO | WO 02/078533 A2 | 10/2002 |
| WO | WO 02/091922 A1 | 11/2002 |
| WO | WO 02/100253 A2 | 12/2002 |
| WO | WO 03/020134 A2 | 3/2003 |
| WO | WO 03/026611 A2 | 4/2003 |
| WO | WO 03/030984 A2 | 4/2003 |
| WO | WO 03/070099 A1 | 8/2003 |
| WO | WO 03/082091 A2 | 10/2003 |
| WO | WO 03/088851 A1 | 10/2003 |
| WO | WO 03/099123 A1 | 12/2003 |
| WO | WO 2004/006928 A1 | 1/2004 |
| WO | WO 2004/022133 A2 | 3/2004 |
| WO | WO 2005/000118 A1 | 1/2005 |
| WO | WO 2005/025413 A2 | 3/2005 |
| WO | WO 2005/084534 A1 | 9/2005 |
| WO | WO 2005/107594 A2 | 11/2005 |
| WO | WO 2005/123173 A1 | 12/2005 |
| WO | WO 2006/003403 A1 | 1/2006 |
| WO | WO 2006/019823 A2 | 2/2006 |
| WO | WO 2006/027586 A1 | 3/2006 |
| WO | WO 2006/111741 A1 | 10/2006 |
| WO | WO 2006/121510 A2 | 11/2006 |
| WO | WO 2006/128034 A1 | 11/2006 |
| WO | WO 2007/002521 A2 | 1/2007 |
| WO | WO 2007/002522 A1 | 1/2007 |
| WO | WO 2007/079530 A1 | 7/2007 |
| WO | WO 2007/097754 A1 | 8/2007 |
| WO | WO 2007/108987 A2 | 9/2007 |
| WO | WO 2007/115291 A2 | 10/2007 |
| WO | WO 2008/016646 A2 | 2/2008 |
| WO | WO 2008/031035 A2 | 3/2008 |
| WO | WO 2008/043156 A1 | 4/2008 |
| WO | WO 2008/052034 A1 | 5/2008 |
| WO | WO 2008/081444 A2 | 7/2008 |
| WO | WO 2008/153930 A1 | 12/2008 |
| WO | WO 2009/004627 A3 | 1/2009 |
| WO | WO 2009/055693 A2 | 4/2009 |
| WO | WO 2009/071775 A1 | 6/2009 |
| WO | WO 2009/104765 A1 | 8/2009 |
| WO | WO 2009/107135 A2 | 9/2009 |
| WO | WO 2009/126653 A1 | 10/2009 |
| WO | WO 2009/149308 A2 | 12/2009 |
| WO | WO 2009/151421 A1 | 12/2009 |
| WO | WO 2010/011641 A2 | 1/2010 |
| WO | WO 2010/101625 A2 | 9/2010 |
| WO | WO 2010/110916 A2 | 9/2010 |
| WO | WO 2011/016019 A1 | 2/2011 |
| WO | WO 2011/053796 A2 | 5/2011 |
| WO | WO 2011/065972 A2 | 6/2011 |
| WO | WO 2011/088214 A2 | 7/2011 |
| WO | WO 2012/064802 A1 | 5/2012 |

OTHER PUBLICATIONS

International Preliminary Report on Patentability for PCT/US2011/044145 mailed Jan. 31, 2013.
International Preliminary Report on Patentability for PCT/US2011/047565 mailed Feb. 28, 2013.
International Preliminary Report on Patentability for PCT/US2011/047581 mailed Feb. 28, 2013.
Office Action mailed Jan. 31, 2013 for U.S. Appl. No. 13/166,451.
Invitation to Pay Additional Fees for PCT/US2009/046333 mailed Sep. 28, 2009.
International Search Report and Written Opinion for PCT/US2009/046333 mailed Dec. 9, 2009.
Invitation to Restrict or Pay Additional Fees, and Where Applicable, Protest Fees for PCT/US2009/046333 mailed Jul. 8, 2010.
International Preliminary Report on Patentability for PCT/US2009/046333 mailed Aug. 31, 2010.
Invitation to Pay Additional Fees for PCT/US2010/000623 mailed Jun. 28, 2010.
International Search Report and Written Opinion for PCT/US2010/000623 mailed Sep. 22, 2010.
International Search Report and Written Opinion for PCT/US2010/000630 mailed Jun. 16, 2011.
Invitation to Pay Additional Fees for PCT/US2010/000630 mailed Jun. 9, 2010.
Invitation to Pay Additional Fees for PCT/US2010/000624 mailed Jun. 2, 2010.
International Search Report and Written Opinion for PCT/US2010/000624 mailed Aug. 18, 2010.
Invitation to Restrict or Pay Additional Fees, and Where Applicable, Protest Fees for PCT/US2010/000624 mailed Jun. 20, 2011.
International Preliminary Report on Patentability for PCT/US2010/000624 mailed Aug. 5, 2011.
Invitation to Pay Additional Fees for PCT/US2010/054723 mailed Mar. 1, 2011.
International Search Report and Written for PCT/US2010/054723 mailed Jul. 12, 2011.
International PreliminaryReport on Patentability for PCT/US2010/054723 mailed May 10, 2012.
Invitation to Pay Additional Fees for PCT/US2010/054741 mailed Feb. 21, 2011.
International Search Report and Written Opinion for PCT/US2010/054741 mailed Apr. 27, 2011.
International Preliminary Report on Patentability for PCT/US2010/054741 mailed May 10, 2012.
Invitation to Pay Additional Fees for PCT/US2010/054725 mailed Feb. 21, 2011.
International Search Report and Written Opinion for PCT/US2010/054725 mailed Jun. 8, 2011.
International Preliminary Report on Patentability for PCT/US2010/054725 mailed May 10, 2012.
International Search Report and Written Opinion for PCT/US2011/022967 mailed Jul. 7, 2011.
International Preliminary Report on Patentability for PCT/US2011/022967 mailed Aug. 9, 2012.
Invitation to Pay Additional Fees for PCT/US2010/003045 mailed Apr. 6, 2011.
International Search Report and Written for PCT/US2010/003045 mailed Jul. 27, 2011.
International Preliminary Report on Patentability for PCT/US2010/003045 mailed Jun. 7, 2012.
Invitation to Pay Additional Fees for PCT/US2011/021134 mailed Apr. 28, 2011.
International Search Report and Written Opinion for PCT/US2011/021134 mailed Oct. 27, 2011.
International Preliminary Report on Patentabiltiy for PCT/US2011/021134 mailed Jul. 26, 2012.
Invitation to Pay Additional Fees for PCT/US2010/000631 mailed Jun. 9, 2010.
International Search Report and Written Opinion for PCT/US2010/000631 mailed Aug. 4, 2010.
Invitation to Restrict or Pay Additional Fees, and Where Applicable, Protest Fees for PCT/US2010/000631 mailed Jun. 20, 2011.
International Preliminary Report on Patentability for PCT/US2010/000631 mailed Aug. 5, 2011.
International Search Report and Written Opinion for PCT/US2011/041430 mailed Jan. 31, 2012.
Invitation to Pay Additional Fees for PCT/US2011/041430 mailed Nov. 4, 2011.
International Search Report and Written Opinion for PCT/US2011/043698 mailed Feb. 23, 2012.

(56) References Cited

OTHER PUBLICATIONS

Invitation to Pay Additional Fee for PCT/US2011/047565 mailed Dec. 2, 2011.
International Search Report and Written Opinion for PCT/US2011/059876 mailed Mar. 28, 2012.
International Search Report and Written Opinion for PCT/US2011/047581 mailed Feb. 22, 2012.
International Preliminary Report on Patentability for PCT/US2011/021131 mailed Jul. 26, 2012.
Invitation to Pay Additional Fees for PCT/US2011/021131 mailed May 23, 2011.
International Search Report and Written Opinion for PCT/US2011/021131 mailed Sep. 30, 2011.
Invitation to Pay Additional Fees mailed Aug. 17, 2012 in connection with PCT/US2012/035191.
International Search Report and Written Opinion mailed Oct. 4, 2012 in connection with PCT/US2012/035191.
Invitation to Pay Additional Fees mailed Aug. 17, 2012 in connection with PCT/US2012/035207.
International Search Report and Written Opinion mailed Oct. 4, 2012 in connection with PCT/US2012/035207.
International Search Report and Written Opinion for PCT/US2012/035152 mailed Aug. 17, 2012.
International Search Report and Written Opinion for PCT/US2012/032846 mailed Jul. 23, 2012.
Invitation to Pay Additional Fees mailed Aug. 17, 2012 in connection with PCT/US2012/035173.
International Search Report and Written Opinion mailed Oct. 4, 2012 in connection with PCT/US2012/035173.
Restriction Requirement mailed May 16, 2012 for U.S. Appl. No. 12/478,756.
Office Action mailed Mar. 26, 2012 for U.S. Appl. No. 12/716,233.
Office Action mailed Jun. 21, 2012 for U.S. Appl. No. 12/716,229.
Office Action mailed Nov. 1, 2012 for U.S. Appl. No. 12/915,789.
Office Action mailed Nov. 1, 2012 for U.S. Appl. No. 12/915,820.
Office Action mailed Apr. 20, 2012 in connection with U.S. Appl. No. 12/953,744.
Office Action mailed Aug. 23, 2012 in connection with U.S. Appl. No. 12/953,744.
Office Action mailed Dec. 22, 2011 in connection with U.S. Appl. No. 12/716,226.
Office Action mailed Jun. 20, 2012 in connection with U.S. Appl. No. 12/716,226.
[No Author Listed] Sof-Tact Manual. Date Unknown. 57 pages. (After reasonable inquiry, the undersigned believes this manual was available beginning 2001, but cannot determine the exact date of this publication. The year of publication is sufficiently earlier than the effective U.S. filing date and priority date so that the particular month and year of publication is not in issue. See MPEP 609.04(a).).
No Author Listed] Greiner Bio-One Preanalytics Catalogue. www.gbo.com/preanalytics. Feb. 2012. 39 pages.
No Author Listed] Safe-T-Fill®: 100% Plastic Capillary Blood Collection Systems. RAM Scientific. [Month of publication not listed] 2003. Last accessed Jun. 28, 2012 at http//www.ramsci.com.
Angell et al., Silicon Micromechanical Devices. Scientific American. 1983;248:44-55.
Aungst et al., Contributions of drug solubilization, partitioning, barrier disruption, and solvent permeation to the enhancement of skin permeation of various compounds with fatty acids and amines. Pharm Res. Jul. 1990;7(7):712-8.
Baroli, Penetration of metallic nanoparticles in human full-thickness skin. J Ind Derm. 2007;127:1701-12. Epub Mar. 22, 2007.
Bina et al., Clinical impact of prandial state, exercise, and site preparation on the equivalence of alternative-site blood glucose testing. Diabetes Care. Apr. 2003;26(4):981-5.
Brown, Encapsulation of glucose oxidase and an oxygen-quenched fluorophore in polyelectrolyte-coated calcium alginate microspheres as optical glucose sensor systems. Biosens Bioelec. 2005;21:212-16. Epub Sep. 17, 2004.

Cormier et al., Transdermal delivery of desmopressin using a coated microneedle array patch system. J Control Release. Jul. 7, 2004;97(3):503-11.
Duffy et al., Rapid Prototyping of Microfluidic Systems and Polydimethylsiloxane. Anal Chem. Dec. 1, 1998;70:4974-84.
Elias, The Microscopic Structure of the Epidermis and Its Derivatives. In: Percutaneous Absorption- Mechanisms- Methodology. Bronaugh et al., eds. Marcell Dekker. 1989;3-12.
Fineberg et al., Use of an automated device for alternative site blood glucose monitoring. Diabetes Care. Jul. 2001;24(7):1217-20.
Gomes et al., Evaluation of nanoparticles loaded with benzopsoralen in rat peritoneal exudate cells. Int J Pharm. Mar. 6, 2007;332(1-2):153-60. Epub Sep. 27, 2007.
Kost et al., Chapter 4. Ultrasound-Mediated Transdermal Drug Delivery. In: Topical Drug Bioavailability Bioequivalance, and Penetration. Shah et al., eds. Plennum, NY. 1993:91-104.
Matriano et al., Macroflux microprojection array patch technology: a new and efficient approach for intracutaneous immunization. Pharm Res. Jan. 2002;19(1):63-70.
McShane, Microcapsules as 'smart tattoo' glucose sensors: engineering systems with enzymes and glucose-binding sensing elements, *Top Fluor. Spec.*, vol. 11, *Glc. Sens.*, p. 131-163.
Mitragotri et al., Sonophoresis: Enhanced Transdermal Drug Delivery by Application of Ultrasound. In: Encl. of Pharm. Tech., vol. 14, Swarbrick, J., Boylan, J., (Eds.), vol. 14, 103-122, 1996.
Rousche et al., A method for pneumatically inserting an array of penetrating electrodes into cortical tissue. Annals of Biomedical Engineering. 1992;20(4):413-22.
Rousche et al., A System for Impact Insertion of a 100 Electrode Array into Cortical Tissue. Annual Intl Conf IEEE Engineer Med Biol Soc. 1990;12(2):O494-95.
Rouse, Effects of mechanical flexion on the penetration of fullerene amino acid-derivatized peptide nanoparticles through skin Nano-Lett. 2007;7:1 155-60. Epub Dec. 6, 2006.
Suk et al., Gene delivery to differentiated neurotypic cells with RGD and HIV Tat peptide functionalized polymeric nanoparticles. Biomaterials. Oct. 2006;27(29):5143-50.
Uhrich, Polymeric systems for controlled drug release. Chem Rev. 1999;99:3181-98. Epub Oct. 26, 1999.
Verbaan et al., Improved piercing of microneedle arrays in dermatomed human skin by an impact insertion method. J Control Release. May 22, 2008;128(1):80-8. Epub Feb. 26, 2008.
Whitesides et al., Soft lithography in biology and biochemistry. Annu Rev Biomed Eng. 2001;3:335-73.
Xia et al., Soft Lithography. Ann Rev Mater Sci. 1998;28:153-84.
Office Action mailed Apr. 9, 2013 for U.S. Appl. No. 13/208,770.
European Office Action mailed Apr. 11, 2013 for Application No. 10777165.1.
Office Action mailed Apr. 26, 2013 in connection with U.S. Appl. No. 12/953,744.
European Search Report mailed Jan. 8, 2013 for Application No. 09759467.5.
Office Action mailed Dec. 7, 2012 for U.S. Appl. No. 12/478,756.
Office Action mailed Dec. 28, 2012 for U.S. Appl. No. 13/166,611.
International Preliminary Report on Patentability for PCT/US2011/041430 mailed Jan. 10, 2013.
Chinese Office Action mailed Jun. 9, 2013 for Application No. 201080055393.6 and English translation thereof.
Chinese Office Action mailed Jun. 4, 2013 for Application No. 201080017375.9 and English translation thereof.
Office Action mailed Jul. 9, 2013 for U.S. Appl. No. 13/456,505.
International Preliminary Report mailed May 23, 2013 for PCT/US2011/059876.
European Office Action mailed May 8, 2013 for Application No. 10708434.5.
Office Action mailed May 14, 2013 for U.S. Appl. No. 12/716,229.
Office Action mailed Apr. 30, 2013 for U.S. Appl. No. 12/915,735.
Office Action mailed May 30, 2013 for U.S. Appl. No. 12/915,820.
Office Action mailed May 20, 2013 for U.S. Appl. No. 13/016,575.
Office Action mailed May 7, 2013 for U.S. Appl. No. 13/680,351.

\* cited by examiner

LOW-PRESSURE PACKAGING FOR FLUID DEVICES

RELATED APPLICATIONS

This application is a continuation of U.S. patent application Ser. No. 13/183,789, filed Jul. 15, 2011, entitled "Low-Pressure Packaging for Fluid Devices," by Schott, which claims the benefit of U.S. Provisional Patent Application Ser. No. 61/365,196, filed Jul. 16, 2010, entitled "Low-Pressure Packaging for Fluid Devices," by Schott, each of which is incorporated herein by reference.

FIELD OF INVENTION

The present invention generally relates to systems and methods for delivering and/or receiving fluid from subjects, e.g., through the skin, including packaging associated with such systems.

BACKGROUND

A variety of techniques and methods exist for sensing and responding to conditions to which a subject is exposed, including sensing of physiological conditions of a mammal and/or a surrounding environment. Other techniques exist for withdrawing a fluid from a mammal, such as blood. While many such techniques are suitable for various purposes, techniques that have one or more features such as added simplicity and flexibility of use would be advantageous.

SUMMARY OF THE INVENTION

The present invention generally relates to systems and methods for delivering and/or receiving fluid from subjects, e.g., through the skin, including packaging associated with such systems. The subject matter of the present invention involves, in some cases, interrelated products, alternative solutions to a particular problem, and/or a plurality of different uses of one or more systems and/or articles.

In one aspect, the present invention is directed to an article. According to one set of embodiments, the article includes an environment having a pressure that is less than about 50 mmHg below atmospheric pressure, where the environment surrounds a device. The device, in some cases, comprises one or more skin insertion objects for withdrawing a substance from the skin and/or from beneath the skin of a subject, and/or for delivering a substance to the skin and/or to a location beneath the skin of a subject.

The article, in another set of embodiments, may be directed to a device contained within a package, where the package contains a first volume defined by the device contained therein and a second volume defined externally of the device. The second volume, in some cases, may be no more than about 25% of the first volume. In some embodiments, the device may comprise one or more skin insertion objects for withdrawing a substance from the skin and/or from beneath the skin of a subject, and/or for delivering a substance to the skin and/or to a location beneath the skin of a subject.

In yet another set of embodiments, the article is directed to a device contained within a package, where the package contains a first volume defined by the device contained therein and a second volume defined externally of the device. The second volume, in some embodiments, can have a volume at least about 50% of the first volume. In some instances, the device may comprise one or more skin insertion objects for withdrawing a substance from the skin and/or from beneath the skin of a subject, and/or for delivering a substance to the skin and/or to a location beneath the skin of a subject.

In yet another set of embodiments, the article may include a device contained within a package substantially molded to the device. The device, in some cases, comprises one or more skin insertion objects for withdrawing a substance from the skin and/or from beneath the skin of a subject, and/or for delivering a substance to the skin and/or to a location beneath the skin of a subject.

Another aspect of the invention is directed to a method. According to one set of embodiments, the method includes an act of exposing a device to an environment having a pressure that is less than about 50 mmHg below atmospheric pressure. In some embodiments, the device comprises one or more skin insertion objects for withdrawing a substance from the skin and/or from beneath the skin of a subject, and/or for delivering a substance to the skin and/or to a location beneath the skin of a subject.

In another aspect, the present invention is directed to a method of making one or more of the embodiments described herein. In another aspect, the present invention is directed to a method of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
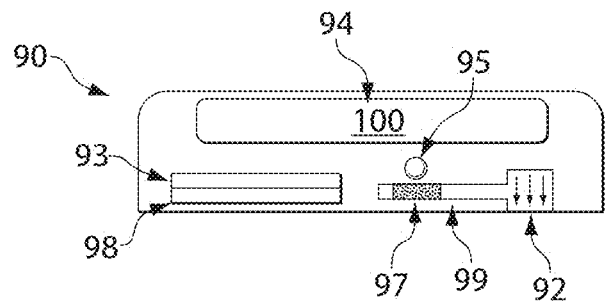
FIGS. 1A-1B illustrate devices according to certain embodiments of the invention.

The present invention generally relates to systems and methods for delivering and/or receiving fluid from subjects, e.g., through the skin, including packaging associated with such systems. Certain aspects of the invention are generally directed to devices for receiving a substance from the skin and/or from beneath the skin of a subject, and/or for delivering a substance to the skin and/or to a location beneath the skin of a subject. In some embodiments, the devices may comprise one or more substance transfer components, such as needles or microneedles. In some cases, the device also may comprise one or more vacuum chambers, e.g., having an internal pressure less than atmospheric pressure. In some aspects, the device may be contained within an environment able to assist with maintenance of such pressures. For example, a package containing such an environment may also have a pressure less than atmospheric pressure, and/or the package may be molded to the device or otherwise have a shape that does not contain substantial gases that can "leak" into the device and alter the pressure of any vacuum chambers that may be contained therein. In some embodiments, the pressure of the environment may be the same as or less than that of vacuum chambers contained within the device. Other aspects of the invention are generally directed to methods of creating such devices, techniques for using such devices, kits involving such devices, and the like.

As mentioned, one aspect of the invention is generally directed to environments for containing devices that may have vacuum chambers having internal pressures less than that of the surrounding atmospheric pressure (about 101 kPa, or about 760 mmHg). It should be understood that the atmospheric pressure may vary somewhat, but is generally around these values. Examples of such devices containing vacuum chambers are discussed in more detail below. In one set of embodiments, the environment containing the device may also have a pressure less than that of atmospheric pressure. For instance, the environment may have a pressure that is at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least 550 mmHg, at least 600 mmHg, at least 650 mmHg, at least about 700 mmHg, or at least about 750 mmHg less than atmospheric pressure.

In some embodiments, the pressure within the environment may be substantially the same as or less than the pressure of any vacuum chambers contained within the device. Without wishing to be bound by any theory, it is believed that the "leakage" or diffusion of gases into a vacuum chamber within the device may be at least partially slowed by having the pressure of the environment surrounding the device to be the same as, or even lower, than the internal pressure within the vacuum chamber. Thus, for example, a lower environmental pressure surrounding the device may, over time, decrease the internal pressure within a vacuum chamber contained within the device.

The pressure of the environment surrounding the device may be created or maintained by any suitable technique. In one set of embodiments, the environment is contained within a package partially or completely surrounding the device. The package may be formed out of any suitable material, and in some cases, out of materials that are substantially gas-impermeable. For example, the package may be formed out of glass, a metal such as stainless steel or aluminum (e.g., as a rigid metal package or as a deformable foil, for instance, aluminum foil), a polymer (for example, polycarbonate, polyvinylidene dichloride (PVDC) or Saran wrap, polypropylene (PP), polyolefin, nylon, a polyethylene such as low density polyethylene (LDPE) or high density polyethylene (HDPE), polyester (PET)), a laminate (e.g., of a metal and a polymer), a metalized film or foil, Mylar, Ofoil™ 48, or the like. Ofoil™ 48 is a laminated rollstock and pouching laminate material available from Oliver-Tolas Healthcare Packaging (Grand Rapids, Mich.). For example, in one embodiment, the package is formed from aluminum foil laminated to an inner polymer layer. The package may be manually deformable (e.g., unaided, without the use of tools), or the package may be rigid and non-manually deformable in some cases. For example, the package may be a hard "shell" or box that contains the device, or at least a portion thereof, or the package may be a bag that surrounds the device.

In one set of embodiments, the package has substantially the same shape as the device contained within the package, e.g., due to the relatively low pressure therein. Thus, the shape of the package may substantially be molded around the device contained therein, at least in some instances. For example, the package may be formed out of a material that does not inherently have a predefined shape (e.g., a bag), but after packaging the material around the device to create a low pressure therein, the material is "held" to the device, thereby forming a shape that is substantially the same shape as the device, due to differences in pressure inside the material relative to atmospheric pressure. In other embodiments, however, the package may be formed from a rigid material, but be formed in a shape (e.g., a predefined shape) that is substantially the same shape of the device.

In some embodiments, the package may have a volume that is no more than about 50%, no more than about 25%, no more than about 20%, no more than about 15%, no more than about 10%, no more than about 5%, no more than about 3%, no more than about 1%, or no more than about 0.5% of the volume of the device contained within the package, thereby providing a tight fit or mold of the package around the device. In other embodiments, however, the volume of the package may be much larger than the volume of the device contained within the package. For instance, the package may have a volume that is at least about 50%, at least about 75%, at least about 100%, at least about 150%, at least about 200%, at least about 300%, at least about 400%, at least about 500%, at least about 600%, at least about 700%, at least about 800%, at least about 900%, or at least about 1000% of the volume of the device contained within the package. In one embodiment, the volume of the package is no more than about 2000% or about 1000% of the volume of the device contained within the package.

In some embodiments, the pressure within the package may be held due to the composition of the package, e.g., the package may be formed out of a substantially gas-impermeable material, such that there is little or no leakage of external (ambient) air into the package. Thus, for example, the permeability of the material to $O_2$, $N_2$, $CO_2$, and/or $H_2O$ may be less than about 2000 cm$^3$ mm/(m$^2$ Bar day) (gas flow in cm$^3$/day for a material having an area given in m$^2$, a thickness in mm, and a pressure difference across the material in Bar), less than about 1500 cm$^3$ mm/(m$^2$ Bar day), less than about 1000 cm$^3$ mm/(m$^2$ Bar day), less than about 900 cm$^3$ mm/(m$^2$ Bar day), less than about 800 cm$^3$ mm/(m$^2$ Bar day), less than about 700 cm$^3$ mm/(m$^2$ Bar day), less than about 600 cm$^3$ mm/(m$^2$ Bar day), less than about 500 cm$^3$ mm/(m$^2$ Bar day), less than about 400 cm$^3$ mm/(m$^2$ Bar day), less than about 300 cm$^3$ mm/(m$^2$ Bar day), less than about 200 cm$^3$ mm/(m$^2$ Bar day), less than about 100 cm$^3$ mm/(m$^2$ Bar day), less than about 90 cm$^3$ mm/(m$^2$ Bar day), less than about 80 cm$^3$ mm/(m$^2$ Bar day), less than about 70 cm$^3$ mm/(m$^2$ Bar day), less than about 60 cm$^3$ mm/(m$^2$ Bar day), less than about 50 cm$^3$ mm/(m$^2$ Bar day), less than about 40 cm$^3$ mm/(m$^2$ Bar day), less than about 30 cm$^3$ mm/(m$^2$ Bar day), less than about 20 cm$^3$ mm/(m$^2$ Bar day), less than about 10 cm$^3$ mm/(m$^2$ Bar day), or less than about 5 cm$^3$ mm/(m$^2$ Bar day), etc. In other embodiments, the pressure within the package may be maintained using active techniques, for example, using a pump to pump gases out of the package (which pump can be run intermittently or continuously, etc.).

Any suitable technique may be used to create and/or maintain the pressure of the environment surrounding the device. For example, vacuum pumps such as rotary vane pumps, diaphragm pumps, liquid ring pumps, piston pumps, screw pumps, scroll pumps, Wankel pumps, external vane pumps, Toepler pumps, or lobe pumps may be used to decrease the pressure of the environment surrounding the device. Many such vacuum pumps are available commercially, and supplied by different manufacturers for different uses. For instance, in one set of embodiments, a device is placed within a package material, then gas within the package material is removed, e.g., using a pump, thereby causing the package material to collapse and generally mold itself onto the exterior surface of the device. In another set of embodiments, the device may be placed within a vacuum packager, such as MultiVac C100 (Multivac, Kansas City, Mo.) which can be used to create a vacuum surrounding the device.

While medical devices are often packaged within sterile environments, i.e., within materials that prevent or at least reduce the ability of microorganisms such as bacteria or viruses from entering the medical device, such packages usually do not contain a reduced pressure environment, i.e., an environment having a pressure less than atmospheric pressure. Packaging able to maintain such pressures must be airtight and substantially impermeable to gases such as $O_2$ (oxygen), $N_2$ (nitrogen), He (helium), etc., rather than only being substantially impermeable to microorganisms, as any transport of gas into an environment having a pressure less than atmospheric pressure will result in loss of the reduced pressure environment, even if sterility is maintained. The dimensions of gases are orders of magnitude smaller than that of microorganisms, so that the requirements for integrity are correspondingly more strict. Thus, a packaging material that is substantially impermeable to microorganisms is not necessarily also substantially impermeable to gases. Moreover, for most prior art medical device applications, reduced pressure environments are undesirable, as even a minor breach in integrity of the package will result in the influx of gases into the package, which may also cause the introduction of microorganisms into the package. Thus, medical devices are typically not packaged within reduced pressure environments having pressures less than atmospheric pressure.

Figure 4A:
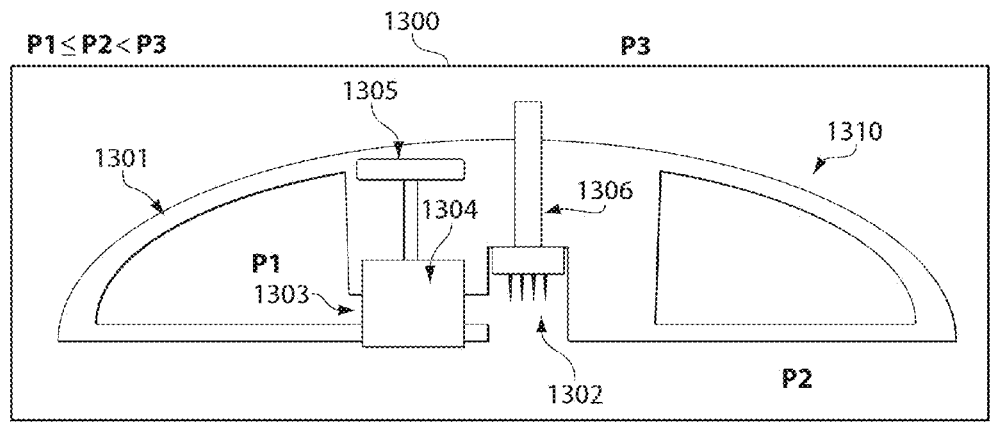
FIGS. 4A-4C illustrate various devices enclosed in packages, according to yet other embodiments of the invention.
Figure 4B:
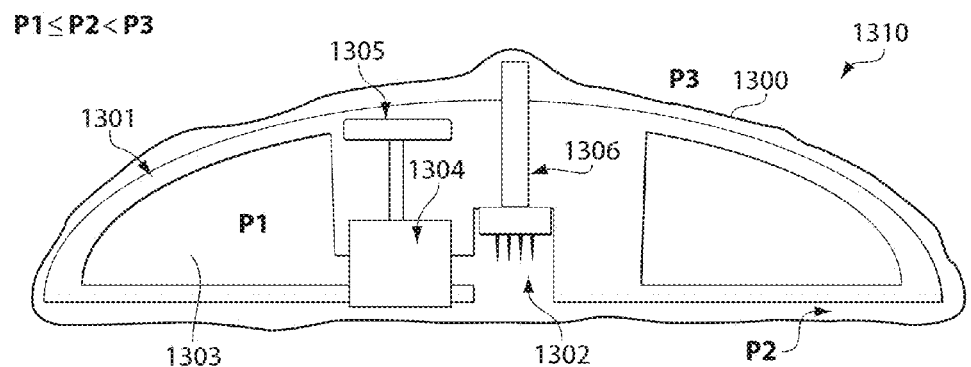
Figure 4C:
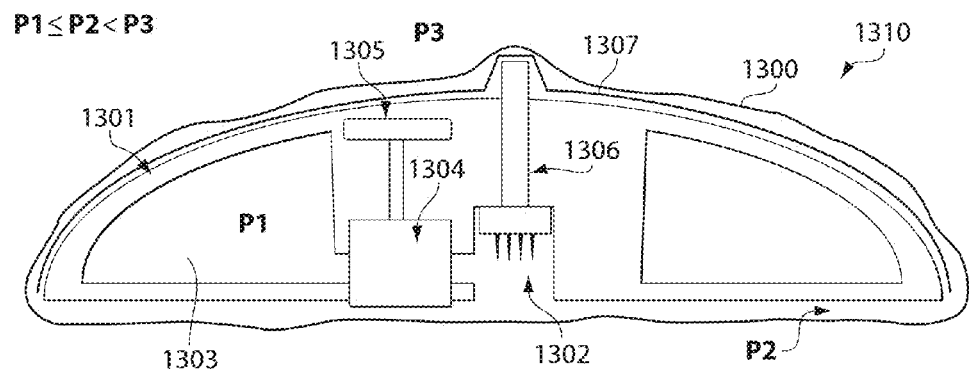

One non-limiting example of such a package is shown with respect to FIG. 4A. In this figure, device 1310 is contained within package 1300. Package 1300 in this embodiment is a rigid package, although in other embodiments such as shown in FIGS. 4B and 4C, package 1300 may be flexible or deformable. In this embodiment, package 1300 contains an environment therein having a pressure P2, which may in some embodiments be less than the external (ambient) pressure P3.

Contained within package 1300 is device 1310, containing support structure 1301, one or more substance transfer components 1302, a pressure regulator 1303, a sensor 1304, a signal or display 1305, and a device activator 1306. For instance, the substance transfer components may include one or more microneedles, such as is shown in FIG. 4A. The activator may be constructed and arranged to cause exposure of the substance transfer components to the skin upon activation of the activator. For example, device activator 1306 may be a button as is shown in FIG. 4A, a dial, a switch, or the like.

Pressure regulator 1303, in this embodiment, includes a vacuum chamber having a first pressure P1. Pressure P1 within device 1310 may be the same as or less than pressure P2 within package 1300, although in other embodiments, pressure P1 may be greater than pressure P2. If pressure P1 is substantially equal to pressure P2, then there would be no tendency for gases to leak or diffuse into or out of pressure regulator 1303 into the surrounding environment. If pressure P1 is less than pressure P2, some gas may have a tendency to diffuse into pressure regulator 1303, while if pressure P1 is greater than pressure P2 then some gas may have a tendency to diffuse out of pressure regulator 1303.

Another embodiment is shown in FIG. 4B, although in this example, a manually deformable material is used as package 1300 (e.g., a bag or a pouch) to contain device 1310, rather than a rigid package as is shown in FIG. 4A. Package 1300 may not have a predefined shape, but may generally adopt the outer shape of the device due to differences in pressure within package 1300 (pressure P2), relative to the external (ambient) pressure P3. For instance, when pressure P2 is less than pressure P3, the external ambient pressure may force package 1300 to adopt a shape that is substantially the same shape as device 1310.

The device as shown in this figure is similar to the one discussed above with reference to FIG. 4A. For instance, device 1310 may contain a pressure regulator 1303 that has a pressure therein P1. Pressure P1 within device 1310 may be the same as or less than pressure P2, although in other embodiments, pressure P1 may be greater than pressure P2. FIG. 4C is similar to FIG. 4B, except in this example, a rigid material 1307 has been added to at least partially contain and/or support device 1310. Such a rigid material may be used, for example, to protect device 1310 against mechanical jostling or handling, and/or to protect accidental activation of the device via device activator 1306, e.g., if device activator 1306 were to be accidentally bumped. For example, rigid material 1307 may have the shape of a shield, a tray, a shell, or the like. Rigid material 1307 may be formed as an integral part of package 1300 and/or device 1310, and/or rigid material 1307 may be a separate component contained within package 1300, as is depicted in the example shown in FIG. 4C. In some cases, the rigid material may be able to yield a lower final vacuum immediately after sealing the package than a flexible package alone.

In some cases, the environment may also be substantially sterile. For example, the package may be formed out of a sterilizable material. For example, the material may be able to withstand sterilizing conditions without significant degradation. For example, the material may be able to withstand one or more sterilization techniques such as chemicals, radiation (for example, with ultraviolet light and/or ionizing radiation), heat-treatment, or the like. Appropriate sterilization techniques and protocols are known to those of ordinary skill in the art. For example, in one embodiment, the material is autoclavable, i.e., the material is able to withstand commonly-used autoclaving conditions (e.g., exposure to temperatures greater than about 100° C. or about 120° C., often at elevated pressures, such as gauge pressures of at least one atmosphere), such that the material, after sterilization, does not substantially deform or otherwise become unusable, e.g., becomes permeable to gases and/or develops holes. Other examples of sterilization techniques include exposure to chemicals such as phenolics, alcohols or alcohol/water mixtures (e.g., isopropanol, isobutanol, ethanol, etc.), halogens (e.g., dissolved chlorine, bromine, etc.), iodine (e.g., a tincture), heavy metals (e.g., silver nitrate, etc.), quaternary ammonium compounds, detergents, aldehydes (e.g., formaldehyde, glutaraldehyde, etc.), gases (e.g., carbon dioxide, ethylene oxide, ozone, etc.), or radiation such as ultraviolet radiation (e.g., at a frequency of about 260 nm), infrared radiation, gamma rays, short wavelength, or high-intensity radiation, such as gamma rays, electron-beams, or X-rays.

It should be noted that the sterilization may not necessarily be total. In some cases, sterilization may be carried out until there is a reduction of at least about $10^6$ in the number of viable organisms present, for instance, through inhibiting or inactivating the organisms. In certain embodiments, the sterilization process may be carried out until there is a reduction of at least about $10^7$, in some cases at least about $10^8$, and in other cases at least about $10^9$ in the number of viable organisms present. In some embodiments, sterilization may be carried out until substantially all of the viable organisms present have been inhibited or inactivated in some fashion, or such that no viable organisms can be detected after sterilization.

In some embodiments, an oxygen scavenger may be present within the package, for example, formed as an integral portion of the package and/or a separate component contained within the package. In one embodiment, the oxygen scavenger may be formed as an integral part of a device contained within the package. In one set of embodiments, the oxygen scavenger may be an oxygen scavenging film. Oxygen scavenging films include PVDC-coated films, incorporation of polyvinyl alcohol (PVOH) as an oxygen barrier layer, or the use of vacuum-deposited aluminum to reduce oxygen penetration to packaging products. Such oxygen scavenging films may be readily obtained commercially, e.g., CSP-1940 and CSP-1941 from CSP Technologies, USA. Yet other examples include those disclosed in U.S. Pat. No. 5,496,649.

For example, such films may be formed from a blend of components. As an example, a first component may include an oxidizable base polymer, poly (ethylene methylacrylate cyclohexenyl methylacrylate) (EMCM). The second component may include a masterbatch comprising a transition metal catalyst and a non-migratory photoinitiator, in addition to a channeling agent and a base polymer. The non-migratory photoinitiator may allow the packager to initiate the $O_2$ scavenging mechanism just prior to filling, which can increase the capacity of the active scavenging component. Upon UV-radiation activation, the polymer system may absorb residual $O_2$ (e.g., via irreversible bonding) in the package headspace, and/or additional $O_2$ that may permeate through the primary packaging barrier.

As mentioned, in certain aspects, the present invention generally relates to devices for receiving a substance from a subject, e.g. received from the skin and/or from beneath the skin of the subject, and/or for delivering a substance to a subject, e.g. delivering a substance to the skin and/or to a location beneath the skin of a subject. Details of such devices follow. The device, in some cases, may be interfaced with external equipment to determine an analyte contained within a fluid contained within or collected by the device. For example, the device may be mounted on an external holder, the device may include a port for transporting fluid out of the device, the device may include a window for interrogating a fluid contained within the device, or the like.

The received fluid may be any suitable bodily fluid, such as interstitial fluid, other skin-associated material, mucosal material or fluid, whole blood, perspiration, saliva, plasma, tears, lymph, urine, plasma, or any other bodily fluid, or combinations thereof. Substances received from a subject can include solid or semi-solid material such as skin, cells, or any other substance from the subject. Substances that can be delivered to a subject in accordance with some embodiments of the invention include diagnostic substances, therapeutic substances such as drugs, and the like. Various embodiments of the invention are described herein in the context of delivering or receiving a fluid, such as blood, from or through the skin. It is to be understood that in all embodiments herein, regardless of the specific exemplary language used (e.g., receiving blood), the devices and methods of other embodiments of the invention can be used for receiving any substance from the skin and/or from beneath the skin of the subject, and/or for delivering any substance to the subject, e.g. to the skin and/or a location beneath the skin of the subject. It should also be understood that, in some cases, fluid may be created beneath the skin, e.g., in the fatty or muscle layers below the skin. Accordingly, descriptions herein of delivering and/or receiving fluid "in the skin" should also be understood to include, in other embodiments, the delivery to and/or reception of fluid from layers directly beneath the skin.

In one aspect, the present invention is generally directed to devices and methods for receiving or extracting blood or other bodily fluids from a subject, e.g., from the skin and/or from beneath the skin, using devices having a substance transfer component (which may include, for example, one or more microneedles and/or other skin insertion objects). The device may also contain, in some embodiments, a storage chamber having an internal pressure less than atmospheric pressure prior to receiving blood or other bodily fluids. In some cases, a portion of the device may pierce the skin of the subject, and fluid can then be delivered and/or received from the subject. The subject is usually human, although non-human subjects may be used in certain instances, for instance, other mammals such as a dog, a cat, a horse, a rabbit, a cow, a pig, a sheep, a goat, a rat (e.g., *Rattus Norvegicus*), a mouse (e.g., *Mus musculus*), a guinea pig, a hamster, a primate (e.g., a monkey, a chimpanzee, a baboon, an ape, a gorilla, etc.), or the like.

In some cases, the device can be applied to the skin, and activated to receive fluid from the subject. The device, or a portion thereof, may then be processed to determine the fluid and/or an analyte within the fluid, alone or with an external apparatus. For example, fluid may be received into the device, and/or the device may contain sensors or agents able to determine the fluid and/or an analyte suspected of being contained in the fluid.

The invention, in one set of embodiments, involves the determination of a condition of a subject. Bodily fluids and/or other material associated with the skin may be analyzed, for instance, as an indication of a past, present and/or future condition of the subject, or to determine conditions that are external to the subject. Determination may occur, for instance, visually, tactilely, by odor, via instrumentation, etc. In one aspect, accordingly, the present invention is generally directed to various devices for delivering and/or receiving blood, or other bodily fluids, from the skin and/or from beneath the skin of a subject. Accordingly, in the description that follows, the discussion of blood is by way of example only, and in other embodiments, other fluids may be received from the skin in addition to and/or instead of blood.

In one set of embodiments, the device includes a substance transfer component able to deliver or receive fluid from the subject. As used herein, "substance transfer component" is any component or combination of components that facilitates movement of a substance or a fluid from one portion of the device to another, and/or from the device to the subject or vice versa. The substance transfer component may include an opening of any size and/or geometry that is constructed to receive fluid into the device. For example, an opening of a substance transfer component may lie in a two-dimensional plane or the opening may include a three-dimensional cavity, hole, groove, slit, etc. In some embodiments, the substance transfer component may also include one or more microneedles or other skin insertion objects, arranged to cause fluid to be released from the subject, e.g., by piercing the skin of a subject.

In some embodiments, if fluid (e.g. blood or interstitial fluid) partially or fully fills an enclosure surrounding a skin insertion or other object, then the enclosure can define at least a part of a substance transfer component. A substance transfer component may include any other suitable fluid transporter or flow activator. Other components including partially or fully enclosed channels, microfluidic channels, tubes, wicking members, vacuum containers, etc. can be, or be part of, a substance transfer component.

The fluid may be received from and/or through the skin of a subject (or other mucosal surface). The substance transfer component may be, for example, one or more needles and/or microneedles, a hygroscopic agent, a cutter or other piercing element, an electrically-assisted system, or the like, e.g., as discussed in detail herein. If needles or microneedles are used, they may be solid or hollow, i.e., blood or other fluid may travel in and/or around the needles or microneedles into the device. In some cases, the needles or microneedles may also be removed from the subject, e.g., after insertion into the skin, for example, to increase the flow of blood or other fluids from the subject. In one set of embodiments, the substance transfer component includes solid needles that are removed from the skin and a cup or channel to direct the flow of blood or other bodily fluids.

In some aspects, the device may include a support structure, such as a housing. The housing may be used, as discussed herein, for applying a substance transfer component to the surface of the skin of the subject, e.g., so that fluid may be delivered and/or received from the skin of the subject. In some cases, the housing may immobilize the substance transfer component such that the substance transfer component cannot move relative to the housing; in other cases, however, the substance transfer component, or a portion thereof, may be able to move relative to the housing. In one embodiment, as a non-limiting example, the substance transfer component is immobilized relative to the housing, and the deployment actuator is positioned within the device such that application of the device to the skin causes at least a portion of the substance transfer component to pierce the skin of the subject. In some cases, the housing encloses a deployment actuator.

In some embodiments, the deployment actuator, or a portion of the deployment actuator, may move from a first position to a second position. For example, the first position may be one where the deployment actuator has attached thereto a substance transfer component that is not in contact the skin (e.g., a skin insertion object of the substance transfer component may be contained within a recess of the substance transfer component), while the second position of the deployment actuator may be one where the substance transfer component does contact the skin, e.g., to pierce the skin. The deployment actuator may be moved using any suitable technique, e.g., manually, mechanically, electromagnetically, using a servo mechanism, or the like. In one set of embodiments, for example, the deployment actuator may be moved from a first position to a second position by pushing a button on the device, which causes the deployment actuator to move (either directly, or through a mechanism linking the button with the deployment actuator). Other mechanisms (e.g., dials, levers, sliders, etc., as discussed herein) may be used in conjunction of or instead of a button. In another set of embodiments, the deployment actuator may be moved from a first position to a second position automatically, for example, upon activation by a computer, upon remote activation, after a period of time has elapsed, or the like. For example, in one embodiment, a servo connected to the deployment actuator is activated electronically, moving the deployment actuator from the first position to the second position. In some cases, the deployment actuator may include a triggering mechanism that initiates deployment.

In some cases, the deployment actuator and/or the substance transfer component may also be moved from the second position to the first position (or to some other position). For example, after fluid has been delivered and/or received from the skin, e.g., using a substance transfer component, the deployment actuator may be moved, which may move the substance transfer component away from contact with the skin. The deployment actuator may be moved from the second position to the first position using any suitable technique, including those described above, and the technique for moving the deployment actuator from the second position to the first position may be the same or different as that moving the deployment actuator from the first position to the second position.

In some cases, the support structure may be able to draw skin towards the substance transfer component. For example, in one set of embodiments, the device may include a vacuum interface or region. The interface or region may be connected with a vacuum source (external and/or internal to the device), and when a vacuum is applied, skin may be drawn towards the device, e.g., for contact with a substance transfer component, such as one or more needles or microneedles.

In some cases, the device includes an interface that is able to apply vacuum to the skin. The interface may be, for example, a suction cup or a circular bowl that is placed on the surface of the skin, and vacuum applied to the interface to create a vacuum. In one set of embodiments, the interface is part of a support structure, as discussed herein. The interface may be formed from any suitable material, e.g., glass, rubber, polymers such as silicone, polyurethane, nitrile rubber, EPDM rubber, neoprene, or the like. In some cases, the seal between the interface and the skin may be enhanced (e.g., reducing leakage), for instance, using vacuum grease, petroleum jelly, a gel, a hydrogel, or the like. In some cases, the interface may be relatively small, for example, having a diameter of less than about 5 cm, less than about 4 cm, less than about 3 cm, less than about 2 cm, less than about 1 cm, less than about 5 mm, less than about 4 mm, less than about 3 mm, less than about 2 mm, or less than about 1 mm. The interface may be circular, although other shapes are also possible, for example, square, star-shaped (having 5, 6, 7, 8, 9, 10, 11, etc. points), tear-drop, oval, rectangular, or the like. In some cases, non-circular shapes may be used since high-energy points, e.g., the points or corners of the shape may enhance or accelerate blister formation. Non-limiting examples of such shapes are shown in FIG. 6. Other non-circular shapes besides these may also be used in other embodiments.

In one set of embodiments, the device includes a deployment actuator able to drive a substance transfer component into the skin, e.g., so that the device can receive a fluid from the skin and/or from beneath the skin of a subject, and/or so that the substance transfer component can deliver a substance to a subject, e.g. deliver a substance to the skin and/or to a location beneath the skin of a subject. The deployment actuator may be a structure that can be deformed using unaided force (e.g., by a human pushing the structure), or other forces (e.g., electrically-applied forces, mechanical interactions or the like), but is able to restore its original shape after the force is removed or at least partially reduced. For example, the structure may restore its original shape spontaneously, or some action (e.g., heating) may be needed to restore the structure to its original shape. In one set of embodiments, the deployment actuator may include a flexible concave member or a reversibly deformable structure that is moveable between a first configuration and a second configuration. The deployment actuator may be formed out a suitable elastic material, in some cases. For instance, the structure may be formed from a plastic, a polymer, a metal, etc. In one set of embodiments, the structure may have a concave or convex shape. For instance, the edges of the structure may be put under compressive stress such that the structure "bows" out to form a concave or convex shape. A person pushing against the concave or convex shape may deform the structure, but after the person stops pushing on the structure, the structure may be able to return to its original concave or convex shape, e.g., spontaneously or with the aid of other forces as previously discussed. In some cases, the device may be bistable, i.e., having two different positions in which the device is stable.

The deployment actuator may be formed from any suitable material, for example, a metal such as stainless steel (e.g., 301, 301LN, 304, 304L, 304LN, 304H, 305, 312, 321, 321H, 316, 316L, 316LN, 316Ti, 317L, 409, 410, 430, 440A, 440B, 440C, 440F, 904L), carbon steel, spring steel, spring brass, phosphor bronze, beryllium copper, titanium, titanium alloy steels, chrome vanadium, nickel alloy steels (e.g., Monel 400, Monel K 500, Inconel 600, Inconel 718, Inconel x 750, etc.), a polymer (e.g., polyvinylchloride, polypropylene, polycarbonate, etc.), a composite or a laminate (e.g., comprising fiberglass, carbon fiber, bamboo, Kevlar, etc.), or the like. The deployment actuator may be of any shape and/or size. For example, the deployment actutar may have a generally domed shape (e.g., as in a snap dome), and be circular (no legs), or the deployment actuator may have other shapes, e.g., oblong, triangular (3 legs), square (4 legs), pentagonal (5 legs), hexagonal (6 legs), spiderlegged, starlike, clover-shaped (with any number of lobes, e.g., 2, 3, 4, 5, etc.), or the like. The deployment actuator may have, in some embodiments, a hole, dimple, or button in the middle. The deployment actuator may also have a serrated disc or a wave shape. In some cases, a substance transfer component may be mounted on the deployment actuator. In other cases, however, a substance transfer component is mounted on a separate structure which is driven or actuated upon movement of the deployment actuator.

In one set of embodiments, the deployment actuator is not planar, and has a portion that can be in a first position (a "cocked" or predeployed position) or a second position (a "fired" or deployed position), optionally separated by a relatively high energy configuration. In some embodiments, the pre-deployed position may be at a higher energy level than the deployed position. In some cases, both the first position and the second position are stable (i.e., the structure is bistable), although conversion between the first position and the second position requires the structure to proceed through an unstable configuration.

According to one set of embodiments, many devices as discussed herein use various techniques for delivering and/or receiving fluid, for example, in connection with substance transfer components, skin insertion objects, or the like. For example, one or more needles and/or microneedles, a hygroscopic agent, a cutter or other piercing element, an electrically-assisted system, or the like may be used in conjunction with a snap dome or other device as described above. Additional examples of such techniques are described herein and/or in the applications incorporated herein. It is to be understood that, generally, fluids may be delivered and/or received in a variety of ways, and various systems and methods for delivering and/or receiving fluid from the skin are discussed below and/or in the applications incorporated herein. In some embodiments, for example, techniques for piercing or altering the surface of the skin to transport a fluid are discussed, for example, using a needle such as a hypodermic needle or microneedles, chemicals applied to the skin (e.g., penetration enhancers), jet injectors or other techniques such as those discussed below, etc.

As an example, in one embodiment, a needle such as a hypodermic needle can be used to deliver and/or receive fluid to or from the skin. Hypodermic needles are well-known to those of ordinary skill in the art, and can be obtained commercially with a range of needle gauges. For example, the needle may be in the 20-30 gauge range, or the needle may be 32 gauge, 33 gauge, 34 gauge, etc.

If needles are present, the needles may be of any suitable size and length, and may be solid or hollow. The needles may have any suitable cross-section (e.g., perpendicular to the direction of penetration), for example, circular, square, oval, elliptical, rectangular, rounded rectangle, triangular, polygonal, hexagonal, irregular, etc. For example, the needle may have a length of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, etc. The needle may also have a largest cross-sectional dimension of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, etc. For example, in one embodiment, the needle may have a rectangular cross section having dimensions of 175 micrometers by 50 micrometers. In one set of embodiments, the needle may have an aspect ratio of length to largest cross-sectional dimension of at least about 2:1, at least about 3:1, at least about 4:1, at least 5:1, at least about 7:1, at least about 10:1, at least about 15:1, at least about 20:1, at least about 25:1, at least about 30:1, etc.

In one embodiment, the needle is a microneedle. As an example, microneedles such as those disclosed in U.S. Pat. No. 6,334,856, issued Jan. 1, 2002, entitled "Microneedle Devices and Methods of Manufacture and Use Thereof," by Allen, et al., may be used to deliver and/or receive fluids or other materials to or from a subject. The microneedles may be hollow or solid, and may be formed from any suitable material, e.g., metals, ceramics, semiconductors, organics, polymers, and/or composites. Examples include, but are not limited to, pharmaceutical grade stainless steel, titanium, nickel, iron, gold, tin, chromium, copper, alloys of these or other metals, silicon, silicon dioxide, and polymers, including polymers of hydroxy acids such as lactic acid and glycolic acid polylactide, polyglycolide, polylactide-co-glycolide, and copolymers with polyethylene glycol, polyanhydrides, polyorthoesters, polyurethanes, polybutyric acid, polyvaleric acid, polylactide-co-caprolactone, polycarbonate, polymethacrylic acid, polyethylenevinyl acetate, polytetrafluorethylene, polymethyl methacrylate, polyacrylic acid, or polyesters.

In some cases, more than one microneedle may be used. For example, arrays of microneedles may be used, and the microneedles may be arranged in the array in any suitable configuration, e.g., periodic, random, etc. In some cases, the array may have 3 or more, 4 or more, 5 or more, 6 or more, 10 or more, 15 or more, 20 or more, 35 or more, 50 or more, 100 or more, or any other suitable number of microneedles. In some embodiments, the device may have at least 3 but no more than 5 needles or microneedles (or other skin insertion objects), at least 6 but no more than 10 needles or microneedles, or at least 11 but no more than 20 needles or microneedles. Typically, a microneedle will have an average cross-sectional dimension (e.g., diameter) of less than about a micron. It should be understood that references to "needle" or "microneedle" as discussed herein are by way of example and ease of presentation only, and that in other embodiments, more than one needle and/or microneedle may be present in any of the descriptions herein.

Those of ordinary skill in the art can arrange needles relative to the skin for these purposes including, in one embodiment, introducing needles into the skin at an angle, relative to the skin's surface, other than 90°, i.e., to introduce a needle or needles into the skin in a slanting fashion so as to limit the depth of penetration. In another embodiment, however, the needles may enter the skin at approximately 90°.

The needles or microneedles may have any suitable length, and the length may be, in some cases, dependent on the application. For example, needles designed to only penetrate the epidermis may be shorter than needles designed to also penetrate the dermis, or to extend beneath the dermis or the skin. In certain embodiments, the microneedles may have a maximum penetration into the skin of no more than about 3 mm, no more than about 2 mm, no more than about 1.75 mm, no more than about 1.5 mm, no more than about 1.25 mm, no more than about 1 mm, no more than about 900 micron, no more than about 800 microns, no more than about 750 microns, no more than about 600 microns, no more than about 500 microns, no more than about 400 microns, no more than about 300 microns, no more than about 200 microns, no more than about 175 microns, no more than about 150 microns, no more than about 125 microns, no more than about 100 microns, no more than about 75 microns, no more than about 50 microns, etc. In certain embodiments, the needles or microneedles may be selected so as to have a maximum insertion depth of at least about 50 micrometers, at least about 100 micrometers, at least about 300 micrometers, at least about 500 micrometers, at least about 1 mm, at least about 2 mm, at least about 3 mm, etc.

In one set of embodiments, the needles (or microneedles) may be coated. For example, the needles may be coated with a substance that is delivered when the needles are inserted into the skin. For instance, the coating may comprise heparin, an anticoagulant, an anti-inflammatory compound, an analgesic, an anti-histamine compound or a vasodilator to assist with the flow of blood from the skin of the subject. The coating may comprise a drug or other therapeutic agent such as those described herein. The drug or other therapeutic agent may be one used for localized delivery (e.g., of or proximate the region to which the coated needles or microneedles are applied), and/or the drug or other therapeutic agent may be one intended for systemic delivery within the subject.

At least some the skin insertion objects may be at least partially coated by a substance such as a drug, analgesic or agent by using dip or spray coating or other suitable technique. Thus, the substance may be delivered to the skin by the substance dissolving or otherwise detaching from the substance transfer component at or in the skin or other subject site. Alternately, the substance may be delivered after a substance transfer component penetrates the subject, e.g., in a way similar to a hypodermic needle. For example, a skin insertion object of the substance transfer component may be inserted into the skin, and a substance may be pumped or pushed through a hole, groove or other channel of the skin insertion object (e.g., by a high pressure gas).

A drug may be any composition which possesses therapeutic, prophylactic, or diagnostic properties in vivo, for example when administered to an animal, including mammals, such as humans. The drug can be for local treatment or for regional or systemic therapy. The drug can be or include a peptide, protein, carbohydrate (including monosaccharides, oligosaccharides, and polysaccharides), nucleoprotein, mucoprotein, lipoprotein, glycoprotein, nucleic acid molecules (including any form of DNA such as cDNA, RNA, or a fragment thereof, oligonucleotides, and genes), nucleotide, nucleoside, lipid, biologically active organic or inorganic molecules, or combination thereof. Examples of suitable therapeutic and/or prophylactic active agents include anti-infectives, analgesics, anti-inflammatories, steroids, decongestants, neuroactive agents, anesthetics, and sedatives. Examples of suitable diagnostic agents include radioactive isotopes and radioopaque agents, metals, gases, labels including chromatographic, fluorescent, or enzymatic labels.

Examples of biologically active polypeptides or proteins include, but are not limited to, glucagon, glucagon-like peptides such as, GLP-1, GLP-2 or other GLP analogs, derivatives or agonists of Glucagon Like Peptides, exendins such as, exendin-3 and exendin-4, derivatives, agonists and analogs thereof, vasoactive intestinal peptide (VIP), immunoglobulins, antibodies, cytokines (e.g., lymphokines, monokines, chemokines), interleukins, macrophage activating factors, interferons, erythropoietin, nucleases, tumor necrosis factor, colony stimulating factors (e.g., G-CSF), insulin, enzymes (e.g., superoxide dismutase, plasminogen activator, etc.), tumor suppressors, blood proteins, hormones and hormone analogs and agonists (e.g., follicle stimulating hormone, growth hormone, adrenocorticotropic hormone, and luteinizing hormone releasing hormone (LHRH)), vaccines (e.g., tumoral, bacterial and viral antigens), antigens, blood coagulation factors, growth factors (NGF and EGF), gastrin, GRH, antibacterial peptides such as defensin, enkephalins, bradykinins, calcitonin and muteins, analogs, truncation, deletion and substitution variants and pharmaceutically acceptable salts of all the foregoing. Suitable analgesics include but are not limited to lidocaine, bupivacaine, and tetracaine. Suitable steroids include but are not limited to cortisone, betamethasone, budesonide and fluticasone.

In one set of embodiments, the needles or microneedles may be used to deliver a drug into the skin of a subject. The needles or microneedles may be at least partially coated, and the coating may comprise a drug or other therapeutic agent such as those described herein. For example, in one set of embodiments, at least about 50%, at least about 60%, at least about 70%, at least about 80%, at least about 90%, or substantially all of a needle or a microneedle may be coated, and one or more than one needle or microneedle may be coated in a device as discussed herein. For instance, at least about 25%, at least about 50%, at least about 60%, at least about 70%, at least about 80%, at least about 90%, or substantially all of the needles or microneedles in a device may comprise a coating.

Without wishing to be bound by any theory, it is believed that, at least in some cases, longer needles or microneedles may be useful for the delivery of a drug or other therapeutic agent. For example, a needle having a greater depth of penetration into the skin may be useful for delivering the drug or other therapeutic agent deeper into the skin, e.g., closer to capillaries within or below the skin, which may minimize the distance the drug needs to travel before being available systemically and allow a more rapid onset of the drug effect. In addition, greater depth of penetration can be useful for delivering greater amounts of drug. A longer needle can have more surface area exposed internally of the subject, relative to a shorter needle (e.g., of the same diameter), and the increased surface area may allow more of the coating containing drug to be exposed internally of the skin. Thus, for example, a greater amount of drug may be delivered per needle or microneedle that enters the skin.

Accordingly, in certain embodiments, relatively long needles or microneedles may be used for the delivery of a drug or other therapeutic agent into the skin, for example. For instance, the average length of the needles or microneedles in the device may be at least about 200 micrometers, at least about 300 micrometers, at least about 400 micrometers, at least about 500 micrometers, at least about 600 micrometers, at least about 750 micrometers, at least about 800 micrometers, at least about 900 micrometers, at least about 1,000 micrometers, at least about 1,200 micrometers, at least about 1,500 micrometers, at least about 1,700 micrometers, or at least about 2,000 micrometers in some embodiments.

Any of a variety of suitable techniques may be used to coat a needle or a microneedle. For instance, the needle or microneedle may be coated by exposing the needles or microneedles to a liquid containing a substance to be coated thereon. For example, the needles or microneedles may be dipped into a liquid, a liquid may be sprayed on or aerosolized onto the needles or microneedles, an electric field may be used to attract a charged liquid onto the needles or microneedles, etc.

In one embodiment, the fluid is delivered and/or received manually, e.g., by manipulating a plunger on a syringe. In another embodiment, the fluid can be delivered and/or received from the skin mechanically or automatically, e.g., using a piston pump or the like. Fluid may also be received into the device using vacuums such as those discussed herein. For example, vacuum may be applied to a conduit, such as a needle, in fluidic communication with a bodily fluid in order to draw up at least a portion of the fluid from the skin. In yet another embodiment, fluid is received using capillary action (e.g., using a microfluidic channel or hypodermic needle having a suitably narrow inner diameter). In still another embodiment, pressure may be applied to force fluid out of the needle.

In some embodiments, a substance is delivered to a subject from a device. In cases where the needle or other skin insertion object is coated with a drug or other substance, the device may deliver the drug or substance to a subject by penetrating the skin with the coated needle. The substance may be delivered to or beneath the skin by the substance dissolving or otherwise detaching from the substance transfer component at the skin or other subject site. The device may or may not cause fluid release from the subject. In some cases, fluid from the subject is not received into the device and a vacuum source is not needed. Also, in some cases, the device may additionally or alternatively deliver a fluid drug or other fluid substance to a subject. The fluid substance may delivered to or beneath the skin through hollow needles that transfer fluid from the device to the subject.

As still another example, pressurized fluids may be used to deliver fluids or other materials into the skin, for instance, using a jet injector or a "hypospray." Typically, such devices produce a high-pressure "jet" of liquid or powder (e.g., a biocompatible liquid, such as saline) that drives material into the skin, and the depth of penetration may be controlled, for instance, by controlling the pressure of the jet. The pressure may come from any suitable source, e.g., a standard gas cylinder or a gas cartridge. A non-limiting example of such a device can be seen in U.S. Pat. No. 4,103,684, issued Aug. 1, 1978, entitled "Hydraulically Powered Hypodermic Injector with Adapters for Reducing and Increasing Fluid Injection Force," by Ismach.

In some embodiments, fluid may be received using a hygroscopic agent applied to the surface of the skin, or proximate the skin. For example, a device as described herein may contain a hygroscopic agent. In some cases, pressure may be applied to drive the hygroscopic agent into the skin. Hygroscopic agents typically are able to attract water from the surrounding environment, for instance, through absorption or adsorption. Non-limiting examples of hygroscopic agents include sugar, honey, glycerol, ethanol, methanol, sulfuric acid, methamphetamine, iodine, many chloride and hydroxide salts, and a variety of other substances. Other examples include, but are not limited to, zinc chloride, calcium chloride, potassium hydroxide, or sodium hydroxide. In some cases, a suitable hygroscopic agent may be chosen based on its physical or reactive properties, e.g., inertness or biocompatibility towards the skin of the subject, depending on the application.

In some embodiments, the device may comprise a cutter able to cut or pierce the surface of the skin. The cutter may comprise any mechanism able to create a path through which fluids may be delivered and/or received from the skin. For example, the cutter may comprise a hypodermic needle, a blade (e.g., a knife blade, a serrated blade, etc.), a piercing element (e.g., a lancet or a solid or a hollow needle), or the like, which can be applied to the skin to create a suitable conduit for the delivery and/or receiving of fluid from the skin. In one embodiment, a cutter is used to create such a pathway and removed, then fluid may be delivered and/or received via this pathway. In another embodiment, the cutter remains in place within the skin, and fluid may be delivered and/or received through a conduit within the cutter.

In some embodiments, fluid may be received using an electric charge. For example, reverse iontophoresis may be used. Without wishing to be bound by any theory, reverse iontophoresis uses a small electric current to drive charged and highly polar compounds across the skin. Since the skin is negatively charged at physiologic pH, it acts as a permselective membrane to cations, and the passage of counterions across the skin induces an electroosmotic solvent flow that may carry neutral molecules in the anode-to-cathode direction. Components in the solvent flow may be analyzed as described elsewhere herein. In some instances, a reverse iontophoresis apparatus may comprise an anode cell and a cathode cell, each in contact with the skin. The anode cell may be filled, for example, with an aqueous buffer solution (i.e., aqueous Tris buffer) having a pH greater than 4 and an electrolyte (i.e. sodium chloride). The cathode cell can be filled with aqueous buffer. As one example, a first electrode (e.g., an anode) can be inserted into the anode cell and a second electrode (e.g., a cathode) can be inserted in the cathode cell. In some embodiments, the electrodes are not in direct contact with the skin.

A current may be applied to induce reverse iontophoresis, thereby receiving a fluid from the skin. The current applied may be, for example, greater than 0.01 mA, greater than 0.3 mA, greater than 0.1 mA, greater than 0.3 mA, greater than 0.5 mA, or greater than 1 mA. It should be understood that currents outside these ranges may be used as well. The current may be applied for a set period of time. For example, the current may be applied for greater than 30 seconds, greater than 1 minute, greater than 5 minutes, greater than 30 minutes, greater than 1 hour, greater than 2 hours, or greater than 5 hours. It should be understood that times outside these ranges may be used as well.

In one set of embodiments, the device may comprise a substance transfer component in the form of an apparatus for ablating the skin. Without wishing to be bound by any theory, it is believed that ablation comprises removing a microscopic patch of stratum corneum (i.e., ablation forms a micropore), thus allowing access to bodily fluids. In some cases, thermal, radiofrequency, and/or laser energy may be used for ablation. In some instances, thermal ablation may be applied using a heating element. Radiofrequency ablation may be carried out using a frequency and energy capable of heating water and/or tissue. A laser may also be used to irradiate a location on the skin to remove a portion. In some embodiments, the heat may be applied in pulses such that a steep temperature gradient exists essentially perpendicular to the surface of the skin. For example, a temperature of at least 100° C., at least 200° C., at least 300° C., or at least 400° C. may be applied for less than 1 second, less than 0.1 seconds, less than 0.01 seconds, less than 0.005 seconds, or less than 0.001 seconds.

In some embodiments, the device may comprise a substance transfer component in the form of a mechanism for taking a solid sample of tissue. For example, a solid tissue sample may be acquired by methods such as scraping the skin or cutting out a portion. Scraping may comprise a reciprocating action whereby an instrument is scraped along the surface of the skin in two or more directions. Scraping can also be accomplished by a rotating action, for example parallel to the surface of the skin and in one direction (i.e., with a roller drum) or parallel to the surface of the skin and in a circular manner (i.e., with a drilling instrument). A cutting mechanism may comprise a blade capable of making one or more incisions and a mechanism for removing a portion of tissue (i.e., by suction or mechanically picking up) or may use a pincer mechanism for cutting out a portion of tissue. A cutting mechanism may also function by a coring action. For example, a hollow cylindrical device can be penetrated into the skin such that a cylindrical core of tissue may be removed. A solid sample may be analyzed directly or may be liquefied prior to analysis. Liquefaction can comprise treatment with organic solvents, enzymatic solutions, surfactants, etc.

The device may also contain, in some embodiments, a vacuum source. In some cases, the vacuum source is one that is self-contained within the device, i.e., the device need not be connected to an external vacuum source (e.g., a house vacuum) during use of the device to receive blood from the skin. For example, in one set of embodiments, the vacuum source may include a vacuum chamber having a pressure less than atmospheric pressure before blood (or other fluid) is received into the device, i.e., the vacuum chamber is at a "negative pressure" (that is, negative relative to atmospheric pressure) or a "vacuum pressure" (or just having a "vacuum"). For example, the vacuum pressure in the vacuum chamber may be at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least about 550 mmHg, at least about 600 mmHg, at least about 650 mmHg, at least about 700 mmHg, or at least about 750 mmHg, i.e., below atmospheric pressure. However, in other embodiments, it should be understood that other pressures may be used and/or that different methods may be used to produce other pressures (greater than or less than atmospheric pressure). As non-limiting examples, an external vacuum or a mechanical device may be used as the vacuum source; various additional examples are discussed in detail herein.

As a specific, non-limiting example, in one embodiment, a device may be used to receive fluid without an external power and/or a vacuum source. Examples of such devices include skin patches, strips, tapes, bandages, or the like. For instance, a skin patch may be contacted with the skin of a subject, and a vacuum created through a change in shape of a portion of the skin patch or other device (e.g., using a shape memory polymer), which may be used to deliver and/or receive fluid from the skin. As a specific example, a shape memory polymer may be shaped to be flat at a first temperature (e.g., room temperature) but curved at a second temperature (e.g., body temperature), and when applied to the skin, the shape memory polymer may alter from a flat shape to a curved shape, thereby creating a vacuum. As another example, a mechanical device may be used to create the vacuum, For example, springs, coils, expanding foam (e.g., from a compressed state), a shape memory polymer, shape memory metal, or the like may be stored in a compressed or wound released upon application to a subject, then released (e.g., unwinding, uncompressing, etc.), to mechanically create the vacuum.

Thus, in some cases, the device is "pre-packaged" with a suitable vacuum source (e.g., a pre-evacuated vacuum chamber); for instance, in one embodiment, the device may be applied to the skin and activated in some fashion to create and/or access the vacuum source. In yet another example, a chemical reaction may be used to create a vacuum, e.g., a reaction in which a gas is produced, which can be harnessed to provide the mechanical force to create a vacuum. In still another example, a component of the device may be able to create a vacuum in the absence of mechanical force. In another example, the device may include a self-contained vacuum actuator, for example, chemical reactants, a deformable structure, a spring, a piston, etc.

In one set of embodiments, the device may be able to create a pressure differential (e.g. a vacuum). The pressure differential may be created by a pressure regulator. As used here, "pressure regulator" is a pressure controller component or system able to create a pressure differential between two or more locations. The pressure differential should be at least sufficient to urge the movement of fluid or other material in accordance with various embodiments of the invention as discussed herein, and the absolute pressures at the two or more locations are not important so long as their differential is appropriate, and their absolute values are reasonable for the purposes discussed herein. For example, the pressure regulator may produce a pressure higher than atmospheric pressure in one location, relative to a lower pressure at another location (atmospheric pressure or some other pressure), where the differential between the pressures is sufficient to urge fluid in accordance with the invention. In another example, the regulator or controller will involve a pressure lower than atmospheric pressure (a vacuum) in one location, and a higher pressure at another location(s) (atmospheric pressure or a different pressure) where the differential between the pressures is sufficient to urge fluid in accordance with the invention. Wherever "vacuum" or "pressure" is used herein, in association with a pressure regulator or pressure differential of the invention, it should be understood that the opposite can be implemented as well, as would be understood by those of ordinary skill in the art, i.e., a vacuum chamber can be replaced in many instances with a pressure chamber, for creating a pressure differential suitable for urging the movement of fluid or other material.

The pressure regulator may be an external source of vacuum (e.g. a lab, clinic, hospital, etc., house vacuum line or external vacuum pump), a mechanical device, a vacuum chamber, pre-packaged vacuum chamber, or the like. In some cases, vacuum may be created manually, e.g., by manipulating a syringe pump, a plunger, or the like, or the low pressure may be created mechanically or automatically, e.g., using a piston pump, a syringe, a bulb, a Venturi tube, manual (mouth) suction, etc., or the like. Vacuum chambers can be used in some embodiments, where the device contains, e.g., regions in which a vacuum exits or can be created (e.g. a variable volume chamber, a change in volume of which will affect vacuum or pressure). A vacuum chamber can include pre-evacuated (i.e., pre-packaged) chambers or regions, and/or self-contained actuators.

A "self-contained" vacuum (or pressure) regulator means one that is associated with (e.g., on or within) the device, e.g. one that defines an integral part of the device, or is a separate component constructed and arranged to be specifically connectable to the particular device to form a pressure differential (i.e., not a connection to an external source of vacuum such as a hospital's, clinic's, or lab's house vacuum line, or a vacuum pump suitable for very general use). In some embodiments, the self-contained vacuum source may be actuated in some fashion to create a vacuum within the device. For instance, the self-contained vacuum source may include a piston, a syringe, a mechanical device such as a vacuum pump able to create a vacuum within the device, and/or chemicals or other reactants that can react to increase or decrease pressure which, with the assistance of mechanical or other means driven by the reaction, can form a pressure differential associated with a pressure regulator. Chemical reaction can also drive mechanical actuation with or without a change in pressure based on the chemical reaction itself. A self-contained vacuum source can also include an expandable foam, a shape memory material, or the like.

One category of self-contained vacuum or pressure regulators of the invention includes self-contained assisted regulators. These are regulators that, upon actuation (e.g., the push of a button, or automatic actuation upon, e.g., removal from a package or urging a device against the skin), a vacuum or pressure associated with the device is formed where the force that pressurizes or evacuates a chamber is not the same as the actuation force. Examples of self-contained assisted regulators include chambers evacuated by expansion driven by a spring triggered by actuation, release of a shape-memory material or expandable material upon actuation, initiation of a chemical reaction upon actuation, or the like.

Another category of self-contained vacuum or pressure regulators of the invention are devices that are not necessarily pre-packaged with pressure or vacuum, but which can be pressurized or evacuated, e.g. by a subject, health care professional at a hospital or clinic prior to use, e.g. by connecting a chamber of the device to a source of vacuum or pressure. For example, the subject, or another person, may actuate the device to create a pressure or vacuum within the device, for example, immediately prior to use of the device.

The vacuum or pressure regulator may be a "pre-packaged" pressure or vacuum chamber in the device when used (i.e., the device can be provided ready for use by a subject or practitioner with an evacuated region on or in the device, without the need for any actuation to form the initial vacuum). A pre-packaged pressure or vacuum chamber regulator can, e.g., be a region evacuated (relative to atmospheric pressure) upon manufacture and/or at some point prior to the point at which it is used by a subject or practitioner. For example, a chamber is evacuated upon manufacture, or after manufacture but before delivery of the device to the user, e.g. the clinician or subject. For instance, in some embodiments, the device contains a vacuum chamber having a vacuum of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least about 550 mmHg, at least about 600 mmHg, at least about 650 mmHg, at least about 700 mmHg, or at least about 750 mmHg below atmospheric pressure.

In one set of embodiments, a device of the present invention may not have an external power and/or a vacuum source. In some cases, the device is "pre-loaded" with a suitable vacuum source; for instance, in one embodiment, the device may be applied to the skin and activated in some fashion to create and/or access the vacuum source. As one example, a device of the present invention may be contacted with the skin of a subject, and a vacuum created through a change in shape of a portion of the device (e.g., using a shape memory polymer), or the device may contain one or more sealed, self-contained vacuum chambers, where a seal is punctured in some manner to create a vacuum. For instance, upon puncturing the seal, a vacuum chamber may be in fluidic communication with a needle, which can be used to move the skin towards the device, receive fluid from the skin, or the like.

As another example, a shape memory polymer may be shaped to be flat at a first temperature (e.g., room temperature) but curved at a second temperature (e.g., body temperature), and when applied to the skin, the shape memory polymer may alter from a flat shape to a curved shape, thereby creating a vacuum. As yet another example, a mechanical device may be used to create the vacuum, For example, springs, coils, expanding foam (e.g., from a compressed state), a shape memory polymer, shape memory metal, or the like may be stored in a compressed or wound released upon application to a subject, then released (e.g., unwinding, uncompressing, etc.), to mechanically create the vacuum. Non-limiting examples of shape-memory polymers and metals include Nitinol, compositions of oligo(epsilon-caprolactone)diol and crystallizable oligo(rho-dioxanone)diol, or compositions of oligo(epsilon-caprolactone)dimethacrylate and n-butyl acrylate.

In yet another example, a chemical reaction may be used to create a vacuum, e.g., a reaction in which a gas is produced, which can be harnessed to provide the mechanical force to create a vacuum. In some embodiments, the device may be used to create a vacuum automatically, once activated, without any external control by a user.

Figure 3:
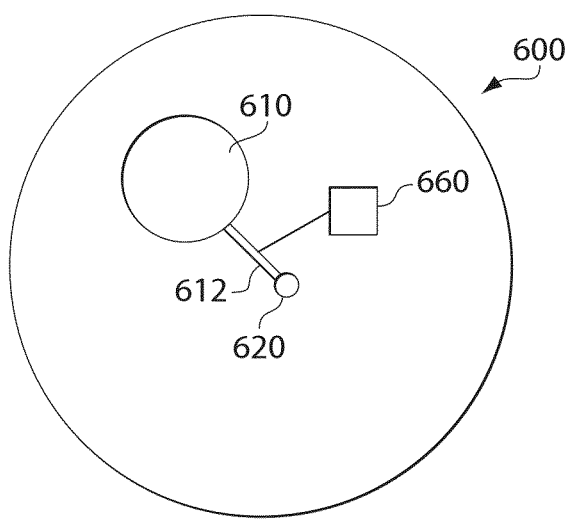
FIG. 3 illustrates a device in one embodiment of the invention, having a vacuum chamber.

In one set of embodiments, the device contains a vacuum chamber that is also used as a storage chamber to receive blood or other fluid received into the device from the subject. For instance, blood received from a subject through or via a substance transfer component may enter the vacuum chamber due to its negative pressure (i.e., because the chamber has an internal pressure less than atmospheric pressure), and optionally stored in the vacuum chamber for later use. A non-limiting example is illustrated in FIG. 3. In this figure, device 600 contains vacuum chamber 610, which is connected to substance transfer component 620 (which may be, e.g., one or more microneedles). Upon activation of vacuum chamber 610 (e.g., using actuator 660, as discussed below), vacuum chamber 610 may be put into fluidic communication with substance transfer component 620. Substance transfer component 620 may accordingly cause negative pressure to be applied to the skin of the subject, for instance, due to the internal pressure within vacuum chamber 610. Fluid (e.g., blood) exciting the skin via substance transfer component 620 may accordingly be drawn into the device and into vacuum chamber 610, e.g., through conduit 612. The fluid collected by the device can then be analyzed within the device or removed from the device for analysis, storage, etc.

In another set of embodiments, however, the device may include separate vacuum chambers and storage chambers (e.g., chambers to store fluid such as blood from the subject). The vacuum chamber and storage chambers may be in fluid communication, and may have any suitable arrangement. In some embodiments, the vacuum from the vacuum chamber may be used, at least in part, to receive fluid from the skin, which is then directed into a storage chamber, e.g., for later analysis or use, for example, as discussed below. As an example, blood may be received into the device, flowing towards a vacuum chamber, but the fluid may be prevented from entering the vacuum chamber. For instance, in certain embodiments, a material permeable to gas but not to a liquid such as blood may be used. For example, the material may be a membrane such as a hydrophilic or hydrophobic membrane having a suitable porosity, a porous structure, a porous ceramic frit, a dissolvable interface (e.g., formed from a salt or a polymer, etc.), or the like.

In certain embodiments, the substance transfer component may be fastened on a deployment actuator. In some cases, the deployment actuator can bring the substance transfer component to the skin, and in certain instances, insert the substance transfer component into the skin. For example, the substance transfer component can be moved mechanically, electrically (e.g., with the aid of a servo, which may be computer-controlled), pneumatically, via a piston, a screw, a mechanical linkage, or the like As mentioned, in some embodiments, blood or other bodily fluids may be stored within the device for later use and/or analysis. For example, the device may be attached to a suitable external apparatus able to analyze a portion of the device (e.g., containing the fluid), and/or the external apparatus may remove at least some of the blood or other fluid from the device for subsequent analysis and/or storage. In some cases, however, at least some analysis may be performed by the device itself, e.g., using one or more sensors, etc., contained within the device.

As mentioned, in one set of embodiments, a device of the invention as discussed herein may be shipped to another location for analysis. In some cases, the device may include an anticoagulant or a stabilizing agent contained within the device, e.g., within a storage chamber for the fluid. Thus, for example, fluid such as blood received from the skin may be delivered to a chamber (e.g., a storage chamber) within the device, then the device, or a portion of the device (e.g., a module) may be shipped to another location for analysis. Any form of shipping may be used, e.g., via mail.

Non-limiting examples of various devices of the invention are shown in FIG. 1. In FIG. 1A, device 90 is used for receiving a fluid from a subject when the device is placed on the skin of a subject. Device 90 includes sensor 95 and substance transfer component 92, e.g., a needle, a microneedle, etc., as discussed herein. In fluidic communication with substance transfer component 92 via fluidic channel 99 is sensing chamber 97. In one embodiment, sensing chamber 97 may contain agents such as particles, enzymes, dyes, etc., for analyzing bodily fluids, such as interstitial fluid or blood. In some cases, fluid may be received using substance transfer component 92 by a vacuum, for example, a self-contained vacuum contained within device 90. Optionally, device 90 also contains a display 94 and associated electronics 93, batteries or other power supplies, etc., which may be used to display sensor readings obtained via sensor 95. In addition, device 90 may also optionally contain memory 98, transmitters for transmitting a signal indicative of sensor 95 to a receiver, etc.

In the example shown in FIG. 1A, device 90 may contain a vacuum source (not shown) that is self-contained within device 90, although in other embodiments, the vacuum source may be external to device 90. (In still other instances, other systems may be used to deliver and/or receive fluid from the skin, as is discussed herein.) In one embodiment, after being placed on the skin of a subject, the skin may be drawn upward into a recess containing fluid transporter 92, for example, upon exposure to the vacuum source. Access to the vacuum source may be controlled by any suitable method, e.g., by piercing a seal or a septum; by opening a valve or moving a gate, etc. For instance, upon activation of device 90, e.g., by the subject, remotely, automatically, etc., the vacuum source may be put into fluidic communication with the recess such that skin is drawn into the recess due to the vacuum. Skin drawn into the recess may come into contact with a skin insertion object (e.g., solid or hollow needles), which may, in some cases, pierce the skin and allow a fluid to be delivered and/or received from the skin. In another embodiment, a skin insertion object may be actuated and moved downward to come into contact with the skin, and optionally retracted after use.

Figure 1B:
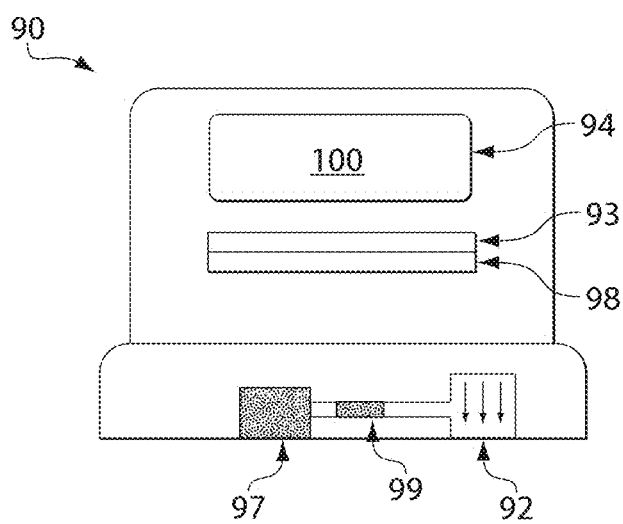

Another non-limiting example of a device is shown in FIG. 1B. This figure illustrates a device useful for delivering a fluid to the subject. Device 90 in this figure includes substance transfer component 92, e.g., including a needle, a microneedle, etc., as discussed herein. In fluidic communication with substance transfer component 92 via fluidic channel 99 is chamber 97, which may contain a drug or other agent to be delivered to the subject. In some cases, fluid may be delivered with a pressure controller, and/or received using substance transfer component 92 by a vacuum, for example, a self-contained vacuum contained within device 90. For instance, upon creating a vacuum, skin may be drawn up towards substance transfer component 92, and substance transfer component 92 may pierce the skin. Fluid from chamber 97 can then be delivered into the skin through fluid channel 99 and substance transfer component 92. Optionally, device 90 also contains a display 94 and associated electronics 93, batteries or other power supplies, etc., which may be used control delivery of fluid to the skin. In addition, device 90 may also optionally contain memory 98, transmitters for transmitting a signal indicative of device 90 or fluid delivery to a receiver, etc.

Figure 2A:
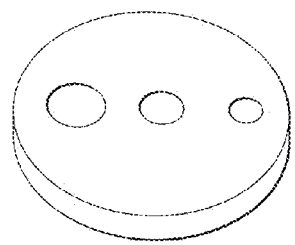
FIGS. 2A-2C illustrate devices according to various embodiments of the invention.
Figure 2B:
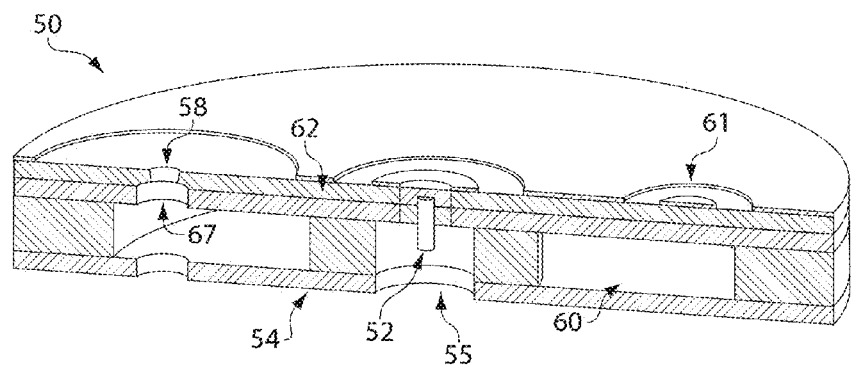

Yet another non-limiting example of a device of the invention is shown in FIG. 2. FIG. 2A illustrates a view of the device (with the cover removed), while FIG. 2B schematically illustrates the device in cross-section. In FIG. 2B, device 50 includes a needle 52 contained within a recess 55. Needle 52 may be solid or hollow, depending on the embodiment. Device 50 also includes a self-contained vacuum chamber 60, which wraps around the central portion of the device where needle 52 and recess 55 are located. A channel 62 connects vacuum chamber 60 with recess 55, separated by a foil or a membrane 67. Also shown in device 50 is button 58. When pushed, button 58 breaks foil 67, thereby connecting vacuum chamber 50 with recess 55, creating a vacuum in recess 55. The vacuum may be used, for example, to draw skin into recess 55, preferably such that it contacts needle 52 and pierces the surface, thereby gaining access to an internal fluid. The fluid may be controlled, for example, by controlling the size of needle 52, and thereby the depth of penetration. For example, the penetration may be limited to the epidermis, e.g., to collect interstitial fluid, or to the dermis, e.g., to collect blood. In some cases, the vacuum may also be used to at least partially secure device 50 on the surface of the skin, and/or to assist in the receiving of fluid from the skin. For instance, fluid may flow into channel 62 under action of the vacuum, and optionally to sensor 61, e.g., for detection of an analyte contained within the fluid. For instance, sensor 61 may produce a color change if an analyte is present, or otherwise produce a detectable signal.

Other components may be added to the example of the device illustrated in FIG. 2, in some embodiments of the invention. For example, device 50 may contain a cover, displays, ports, transmitters, sensors, channels such as microfluidic channels, chambers, and/or various electronics, e.g., to control or monitor fluid transport into or out of device 50, to determine an analyte present within a fluid delivered and/or received from the skin, to determine the status of the device, to report or transmit information regarding the device and/or analytes, or the like, as is discussed in more detail herein. As another example, device 50 may contain an adhesive, e.g., on surface 54, for adhesion of the device to the skin.

Figure 2C:
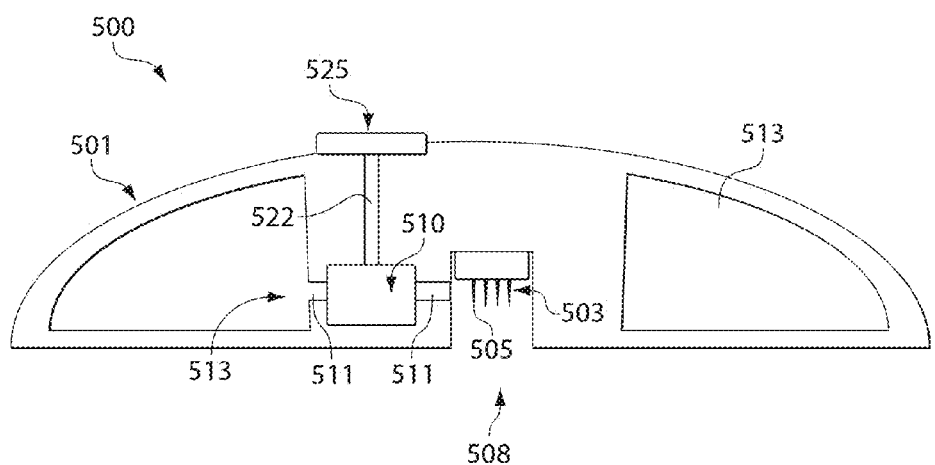

Yet another non-limiting example is illustrated with reference to FIG. 2C. In this example, device 500 includes a support structure 501, and an associated substance transfer component 503. Substance transfer component 503 includes a plurality of needles or microneedles 505, although other skin insertion objects or flow activators as discussed herein may also be used. Also shown in FIG. 2C is sensor 510, connected via channels 511 to recess 508 containing needles or microneedles 505. Chamber 513 may be a self-contained vacuum chamber, and chamber 513 may be in fluidic communication with recess 508 via channel 511, for example, as controlled by a controller or an actuator (not shown). In this figure, device 500 also contains display 525, which is connected to sensor 510 via electrical connection 522. As an example of use of device 500, when fluid is drawn from the skin (e.g., blood, interstitial fluid, etc.), the fluid may flow through channel 511 to be determined by sensor 510, e.g., due to action of the vacuum from vacuum chamber 513. In some cases, the vacuum is used, for example, to draw skin into recess 508, preferably such that it contacts needles or microneedles 505 and pierces the surface of the skin to gain access to a fluid internal of the subject, such as blood or interstitial fluid, etc. The fluid may be controlled, for example, by controlling the size of needle 505, and thereby the depth of penetration. For example, the penetration may be limited to the epidermis, e.g., to collect interstitial fluid, or to the dermis, e.g., to collect blood. Upon determination of the fluid and/or an analyte present or suspected to be present within the fluid, a microprocessor or other controller may display on display 525 a suitable signal. As is discussed below, a display is shown in this figure by way of example only; in other embodiments, no display may be present, or other signals may be used, for example, lights, smell, sound, feel, taste, or the like.

In some embodiments, the device may be an electrical and/or a mechanical device applicable or affixable to the surface of the skin, e.g., using adhesive, or other techniques such as those described herein. The adhesive may be permanent or temporary, and may be used to affix the device to the surface of the skin. The adhesive may be any suitable adhesive, for example, a pressure sensitive adhesive, a contact adhesive, a permanent adhesive, a hydrogel, a cyanoacrylate, a glue, a gum, hot melts, an epoxy, or the like. In some cases, the adhesive is chosen to be biocompatible or hypoallergenic.

In another set of embodiments, the device may be mechanically held to the skin, for example, the device may include mechanical elements such as straps, belts, buckles, strings, ties, elastic bands, or the like. For example, a strap may be worn around the device to hold the device in place against the skin of the subject. In yet another set of embodiments, a combination of these and/or other techniques may be used. As one non-limiting example, the device may be affixed to a subject's arm or leg using adhesive and a strap.

In other embodiments, however, at least a portion of the device may be inserted into the skin, for example, mechanically. For example, in one embodiment, the device may include a cutter, such as a hypodermic needle, a knife blade, a piercing element (e.g., a solid or hollow needle), or the like, as discussed herein. In some cases, the device may comprise a cutter able to cut or pierce the surface of the skin. The cutter may comprise any mechanism able to create a path to a fluid within the skin, e.g., through which fluids may be delivered and/or removed from the skin. For example, the cutter may comprise a hypodermic needle, a knife blade, a piercing element (e.g., a solid or a hollow needle), or the like, which can be applied to the skin to create a suitable conduit for the receiving of fluid from the skin. In one embodiment, a cutter is used to create such a pathway and removed, then fluid is removed via this pathway using any suitable technique. In another embodiment, the cutter remains in place within the skin, and fluid may be drawn through a conduit within the cutter.

Any or all of the arrangements described herein can be provided proximate a subject, for example on or proximate a subject's skin. Activation of the devices can be carried out in a variety of ways. In one embodiment, a device can be applied to a subject and a region of the device activated (e.g., pushed, pressed, or tapped by a user) to inject a needle or a microneedle so as to access interstitial fluid. The same or a different tapping or pushing action can activate a vacuum source, open and/or close one or more of a variety of valves, or the like. The device can be a simple one in which it is applied to the skin and operates automatically (where e.g., application to the skin accesses interstitial fluid and draws interstitial fluid into an analysis region) or the device can be applied to the skin and one tapping or other activation can cause fluid to flow through administration of a needle or a microneedle, opening of a valve, activation of vacuum, or any combination. Any number of activation protocols can be carried out by a user repeatedly pushing or tapping a location or selectively, sequentially, and/or periodically activating a variety of switches. In another arrangement, activation of needles or microneedles, creation of suction blisters, opening and/or closing of valves, and other techniques to facilitate one or more analysis can be carried out electronically or in other manners facilitated by the subject or by an outside controlling entity. For example, a device or patch can be provided proximate a subject's skin and a radio frequency, electromagnetic, or other signal can be provided by a nearby controller or a distant source to activate any of the needles, blister devices, valves or other components of the devices described so that any assay or assays can be carried out as desired.

In some embodiments, fluid may be delivered to the subject, and such fluids may contain materials useful for delivery, e.g., forming at least a portion of the fluid, dissolved within the fluid, carried by the fluid (e.g., suspended or dispersed), or the like. Examples of suitable materials include, but are not limited to, particles such as microparticles or nanoparticles, a chemical, a drug or a therapeutic agent, a diagnostic agent, a carrier, or the like.

As used herein, the term "fluid" generally refers to a substance that tends to flow and to conform to the outline of its container. Typically, fluids are materials that are unable to withstand a static shear stress, and when a shear stress is applied, the fluid experiences a continuing and permanent distortion. The fluid may have any suitable viscosity that permits at least some flow of the fluid. Non-limiting examples of fluids include liquids and gases, but may also include free-flowing solid particles, viscoelastic fluids, and the like. For example, the fluid may include a flowable matrix or a gel, e.g., formed from biodegradable and/or biocompatible material such as polylactic acid, polyglycolic acid, poly(lactic-co-glycolic acid), etc., or other similar materials.

In some cases, fluids or other materials delivered to the subject may be used for indication of a past, present and/or future condition of the subject. Thus, the condition of the subject to be determined may be one that is currently existing in the subject, and/or one that is not currently existing, but the subject is susceptible or otherwise is at an increased risk to that condition. The condition may be a medical condition, e.g., diabetes or cancer, or other physiological conditions, such as dehydration, pregnancy, illicit drug use, or the like. In one set of embodiments, the materials may include a diagnostic agent, for example, one which can determine an analyte within the subject, e.g., one that is a marker for a disease state. As a specific non-limiting example, material delivered to the skin, e.g., to the dermis or epidermis, to a pooled region of fluid, etc., of a subject may include a particle including an antibody directed at a marker produced by bacteria.

In other cases, however, the materials delivered to the subject may be used to determine conditions that are external to the subject. For example, the materials may contain reaction entities able to recognize pathogens or other environmental conditions surrounding the subject, for example, an antibody able to recognize an external pathogen (or pathogen marker).

According to one aspect of the invention, the device is of a relatively small size. In some embodiments, the device may be sized such that it is wearable and/or carryable by a subject. For example, the device may be self-contained, needing no wires, cables, tubes, external structural elements, or other external support. The device may be positioned on any suitable position of the subject, for example, on the arm or leg, on the back, on the abdomen, etc. As mentioned, in some embodiments, the device may be affixed or held onto the surface of the skin using any suitable technique, e.g., using adhesives, mechanical elements such as straps, belts, buckles, strings, ties, elastic bands, or the like. In some cases, the device may be positioned on the subject such that the subject is able to move around (e.g., walking, exercising, typing, writing, drinking or eating, using the bathroom, etc.) while wearing the device. For example, the device may have a mass and/or dimensions such that the subject is able to wear the device for at least about 5 minutes, and in some cases for longer periods of time, e.g., at least about 10 minutes, at least about 15 minutes, at least about 30 minutes, at least about 45 minutes, at least about 1 hour, at least about 3 hours, at least 5 hours, at least about 8 hours, at least about 1 day, at least about 2 days, at least about 4 days, at least about 1 week, at least about 2 weeks, at least about 4 weeks, etc.

In some embodiments, the device is relatively lightweight. For example, the device may have a mass of no more than about 1 kg, no more than about 300 g, no more than about 150 g, no more than about 100 g, no more than about 50 g, no more than about 30 g, no more than about 25 g, no more than about 20 g, no more than about 10 g, no more than about 5 g, or no more than about 2 g. For instance, in various embodiments, the device has a mass of between about 2 g and about 25 g, a mass of between about 2 g and about 10 g, a mass of between 10 g and about 50 g, a mass of between about 30 g and about 150 g, etc.

The device, in some cases, may be relatively small. For example, the device may be constructed and arranged to lie relatively close to the skin. Thus, for instance, the device may have a largest vertical dimension, extending from the skin of the subject when the device is positioned on the skin, of no more than about 25 cm, no more than about 10 cm, no more than about 7 cm, no more than about 5 cm, no more than about 3 cm, no more than about 2 cm, no more than about 1 cm, no more than about 8 mm, no more than about 5 mm, no more than about 3 mm, no more than about 2 mm, no more than about 1 mm, or no more than about 0.5 mm. In some cases, the device may have a largest vertical dimension of between about 0.5 cm and about 1 cm, between about 2 and about 3 cm, between about 2.5 cm and about 5 cm, between about 2 cm and about 7 cm, between about 0.5 mm and about 7 cm, etc.

In another set of embodiments, the device may have a relatively small size. For example, the device may have a largest lateral dimension (e.g., parallel to the skin) of no more than about 25 cm, no more than about 10 cm, no more than about 7 cm, no more than about 5 cm, no more than about 3 cm, no more than about 2 cm, or no more than about 1 cm. In some cases, the device may have a largest lateral dimension of between about 0.5 cm and about 1 cm, between about 2 and about 3 cm, between about 2.5 cm and about 5 cm, between about 2 cm and about 7 cm, etc.

Combinations of these and/or other dimensions are also possible in other embodiments. As non-limiting examples, the device may have a largest lateral dimension of no more than about 5 cm, a largest vertical dimension of no more than about 1 cm, and a mass of no more than about 25 g; or the device may have a largest lateral dimension of no more than about 5 cm, a largest vertical dimension of no more than about 1 cm, and a mass of no more than about 25 g; etc.

The device may be activated, for example, by pushing a button, pressing a switch, moving a slider, turning a dial, or the like. The subject, and/or another person, may activate the device activator. In some cases, the device may be remotely activated. For example, a health care provider may send an electromagnetic signal which is received by the device in order to activate the device, e.g., a wireless signal, a radio signal, etc.

In one set of embodiments, the device may include channels such as microfluidic channels, which may be used to deliver and/or receive fluids and/or other materials into or out of the skin. In some cases, the microfluidic channels are in fluid communication with a substance transfer component that is used to deliver and/or receive fluids to or from the skin. For example, in one set of embodiments, the device may include a hypodermic needle that can be inserted into the skin, and fluid may be delivered into the skin via the needle and/or received from the skin via the needle. The device may also include one or more microfluidic channels to contain fluid for delivery to the needle, e.g., from a source of fluid, and/or to receive fluid from the skin, e.g., for delivery to an analytical chamber within the device, to a reservoir for later analysis, or the like.

In some cases, more than one chamber may be present within the device, and in some cases, some or all of the chambers may be in fluidic communication, e.g., via channels such as microfluidic channels. In various embodiments, a variety of chambers and/or channels may be present within the device, depending on the application. For example, the device may contain chambers for sensing an analyte, chambers for holding reagents, chambers for controlling temperature, chambers for controlling pH or other conditions, chambers for creating or buffering pressure or vacuum, chambers for controlling or dampening fluid flow, mixing chambers, or the like.

Thus, in one set of embodiments, the device may include a microfluidic channel. As used herein, "microfluidic," "microscopic," "microscale," the "micro-" prefix (for example, as in "microchannel"), and the like generally refers to elements or articles having widths or diameters of less than about 1 mm, and less than about 100 microns (micrometers) in some cases.

In some embodiments, larger channels may be used instead of, or in conjunction with, microfluidic channels for any of the embodiments discussed herein. For examples, channels having widths or diameters of less than about 10 mm, less than about 9 mm, less than about 8 mm, less than about 7 mm, less than about 6 mm, less than about 5 mm, less than about 4 mm, less than about 3 mm, or less than about 2 mm may be used in certain instances. In some cases, the element or article includes a channel through which a fluid can flow. In all embodiments, specified widths can be a smallest width (i.e. a width as specified where, at that location, the article can have a larger width in a different dimension), or a largest width (i.e. where, at that location, the article has a width that is no wider than as specified, but can have a length that is greater). Thus, for instance, the microfluidic channel may have an average cross-sectional dimension (e.g., perpendicular to the direction of flow of fluid in the microfluidic channel) of less than about 1 mm, less than about 500 microns, less than about 300 microns, or less than about 100 microns. In some cases, the microfluidic channel may have an average diameter of less than about 60 microns, less than about 50 microns, less than about 40 microns, less than about 30 microns, less than about 25 microns, less than about 10 microns, less than about 5 microns, less than about 3 microns, or less than about 1 micron.

A "channel," as used herein, means a feature on or in an article (e.g., a substrate) that at least partially directs the flow of a fluid. In some cases, the channel may be formed, at least in part, by a single component, e.g. an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

A channel may have any aspect ratio, e.g., an aspect ratio (length to average cross-sectional dimension) of at least about 2:1, more typically at least about 3:1, at least about 5:1, at least about 10:1, etc. As used herein, a "cross-sectional dimension," in reference to a fluidic or microfluidic channel, is measured in a direction generally perpendicular to fluid flow within the channel. A channel generally will include characteristics that facilitate control over fluid transport, e.g., structural characteristics and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases. In one embodiment, the channel is a capillary.

In some cases, the device may contain one or more chambers or reservoirs for holding fluid. In some cases, the chambers may be in fluidic communication with one or more fluid transporters and/or one or more microfluidic channels. For instance, the device may contain a chamber for collecting fluid received from a subject (e.g., for storage and/or later analysis), a chamber for containing a fluid for delivery to the subject (e.g., blood, saline, optionally containing drugs, hormones, vitamins, pharmaceutical agents, or the like), etc.

After receipt of the fluid into the device, the device, or a portion thereof, may be removed from the skin of the subject, e.g., by the subject or by another person. For example, the entire device may be removed, or a portion of the device containing the storage reservoir may be removed from the device, and optionally replaced with another storage reservoir. Thus, for instance, in one embodiment, the device may contain two or more modules, for example, a first module that is able to cause receiving of fluid from the skin into a storage reservoir, and a second module containing the storage module. In some cases, the module containing the storage reservoir may be removed from the device. Other examples of modules and modular systems are discussed below; other examples are discussed in U.S. Provisional Patent Application Ser. No. 61/256,931, filed Oct. 30, 2009, entitled "Modular Systems for Application to the Skin," incorporated by reference herein in its entirety.

The received fluid may then be sent to a clinical and/or laboratory setting, e.g., for analysis. In some embodiments, the entire device may be sent to the clinical and/or laboratory setting; in other embodiments, however, only a portion of the device (e.g., a module containing a storage reservoir containing the fluid) may be sent to the clinical and/or laboratory setting. In some cases, the fluid may be shipped using any suitable technique (e.g., by mail, by hand, etc.). In certain instances, the subject may give the fluid to appropriate personnel at a clinical visit. For instance, a doctor may prescribe a device as discussed above for use by the subject, and at the next doctor visit, the subject may give the doctor the received fluid, e.g., contained within a device or module.

A variety of materials and methods, according to certain aspects of the invention, can be used to form the device, e.g., microfluidic channels, chambers, etc. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American,* 248:44-55, 1983 (Angell, et al).

In one set of embodiments, various components of the systems and devices of the invention can be formed of a polymer, for example, an elastomeric polymer such as polydimethylsiloxane ("PDMS"), polytetrafluoroethylene ("PTFE" or Teflon®), or the like. For instance, according to one embodiment, a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the *Annual Review of Material Science,* 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the *Annual Review of Biomedical Engineering,* 2001, Vol. 3, pages 335-373; each of these references is incorporated herein by reference).

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a fluorinated derivative of a polyimide, or the like. Combinations, copolymers, or blends involving polymers including those described above are also envisioned. The device may also be formed from composite materials, for example, a composite of a polymer and a semiconductor material.

In some embodiments, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, metals, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

As described herein, any of a variety of signaling or display methods, associated with analyses, can be provided including signaling visually, by smell, sound, feel, taste, or the like, in one set of embodiments. Signal structures or generators include, but are not limited to, displays (visual, LED, light, etc.), speakers, chemical-releasing chambers (e.g., containing a volatile chemical), mechanical devices, heaters, coolers, or the like. In some cases, the signal structure or generator may be integral with the device (e.g., integrally connected with a support structure for application to the skin of the subject, e.g., containing a fluid transporter such as a needle or a microneedle), or the signal structure may not be integrally connected with the support structure. As used herein, a "signal structure" or a "signal generator" is any apparatus able to generate a signal that is related to a condition of a medium. For example, the medium may be a bodily fluid, such as blood or interstitial fluid.

In another aspect, the present invention is directed to a kit including one or more of the compositions previously discussed, e.g., a kit including a device for the delivery and/or receiving of fluid from the skin, a kit including a device able to create a pooled region of fluid within the skin of a subject, a kit including a device able to determine a fluid, or the like. A "kit," as used herein, typically defines a package or an assembly including one or more of the compositions or devices of the invention, and/or other compositions or devices associated with the invention, for example, as previously described. For example, in one set of embodiments, the kit may include a device and one or more compositions for use with the device. Each of the compositions of the kit, if present, may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In some embodiments, the present invention is directed to methods of promoting one or more embodiments of the invention as discussed herein. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, repairing, replacing, insuring, suing, patenting, or the like that are associated with the systems, devices, apparatuses, articles, methods, compositions, kits, etc. of the invention as discussed herein. Methods of promotion can be performed by any party including, but not limited to, personal parties, businesses (public or private), partnerships, corporations, trusts, contractual or sub-contractual agencies, educational institutions such as colleges and universities, research institutions, hospitals or other clinical institutions, governmental agencies, etc. Promotional activities may include communications of any form (e.g., written, oral, and/or electronic communications, such as, but not limited to, e-mail, telephonic, Internet, Web-based, etc.) that are clearly associated with the invention.

In one set of embodiments, the method of promotion may involve one or more instructions. As used herein, "instructions" can define a component of instructional utility (e.g., directions, guides, warnings, labels, notes, FAQs or "frequently asked questions," etc.), and typically involve written instructions on or associated with the invention and/or with the packaging of the invention. Instructions can also include instructional communications in any form (e.g., oral, electronic, audible, digital, optical, visual, etc.), provided in any manner such that a user will clearly recognize that the instructions are to be associated with the invention, e.g., as discussed herein.

The following documents are incorporated herein by reference: U.S. patent application Ser. No. 12/478,756, filed Jun. 4, 2009, entitled "Compositions and Methods for Rapid One-Step Diagnosis," by D. Levinson, published as U.S. Patent Application Publication No. 2010/0069726 on Mar. 18, 2010; International Patent Application No. PCT/US09/046,333, filed Jun. 4, 2009, entitled "Compositions and Methods for Rapid One-Step Diagnosis," by D. Levinson, published as WO 2009/149308 on Dec. 10, 2009; U.S. patent application Ser. No. 12/716,233, filed Mar. 2, 2010, entitled "Systems and Methods for Creating and Using Suction Blisters or Other Pooled Regions of Fluid within the Skin," by Levinson, et al.; U.S. patent application Ser. No. 12/716,222, filed Mar. 2, 2010, entitled "Oxygen Sensor," by Levinson, et al.; U.S. patent application Ser. No. 12/716,229, filed Mar. 2, 2010, entitled "Devices and Techniques Associated with Diagnostics, Therapies, and Other Applications, Including Skin-Associated Applications," by Bernstein, et al.; U.S. patent application Ser. No. 12/716,226, filed Mar. 2, 2010, entitled "Techniques and Devices Associated with Blood Sampling," by Levinson, et al.; U.S. Provisional Patent Application Ser. No. 61/294,543, filed Jan. 13, 2010, entitled "Blood Sampling Device and Method," by Chickering, et al.; U.S. Provisional Patent Application Ser. No. 61/334,533, filed May 13, 2010, entitled "Rapid Delivery and/or Withdrawal of Fluids," by Chickering, et al.; and U.S. Provisional Patent Application Ser. No. 61/334,529, filed May 13, 2010, entitled "Sampling Device Interfaces," by Chickering, et al. In addition, U.S. Provisional Patent Application Ser. No. 61/365,196, filed Jul. 16, 2010, entitled "Low-Pressure Packaging for Fluid Devices," by Schott, is incorporated herein by reference.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
a receiving device for receiving blood and/or other bodily fluid from the skin and/or from beneath the skin of a subject, comprising at least one microneedle and a vacuum chamber containing therein a first reduced pressure that is less than about 50 mmHg below atmospheric pressure;
a package containing therein the receiving device, the package comprising a material having a permeability to $O_2$ or $N_2$ of less than about 2000 $cm^3$ mm/($m^2$ Bar day) and having an inner surface; and
a second reduced pressure between the receiving device and the inner surface of the package, wherein the second reduced pressure is less than about 50 mmHg below atmospheric pressure.

2. The article of claim 1, wherein one or more of the at least one microneedles is solid.

3. The article of claim 1, wherein at least a portion of the package is manually deformable.

4. The article of claim 1, wherein at least a portion of the package is rigid.

5. The article of claim 1, wherein the package comprises a laminate of a metal and a polymer.

6. The article of claim 5, wherein the laminate comprises aluminum foil that is laminated to the polymer.

7. The article of claim 5, wherein the polymer is polyester.

8. The article of claim 1, wherein the first reduced pressure is less than about 500 mmHg below atmospheric pressure, and the second reduced pressure is less than about 500 mmHg below atmospheric pressure.

9. The article of claim 1, wherein the pressure of the vacuum chamber and the pressure of the package are substantially equal.

10. The article of claim 1, wherein the receiving device defines therein a first volume, and the package defines therein a second volume defined externally of the receiving device, wherein the second volume is no more than about 25% of the first volume.

11. The article of claim 1, wherein the receiving device defines therein a first volume, and the package defines therein a second volume defined externally of the receiving device, wherein the second volume is at least about 50% of the first volume.

12. The article of claim 1, wherein the package contains a sterile environment.

13. The article of claim 1, wherein the package further comprises an oxygen scavenger.

14. The article of claim 13, wherein the oxygen scavenger is an oxygen scavenging film contained within the material of the package.

15. The article of claim 1, wherein the material of the package further comprises an oxygen barrier layer.

16. The article of claim 1, wherein the receiving device further comprises a device activator that, when the device activator is activated, applies the reduced pressure from the vacuum chamber to the skin of the subject to cause blood and/or other bodily fluids released from the subject due to action of the at least one microneedle to flow, from the subject, into the receiving device.

* * * * *